(12) United States Patent
Carstensen et al.

(10) Patent No.: US 11,058,129 B2
(45) Date of Patent: Jul. 13, 2021

(54) ANIMAL FEED ADDITIVES

(71) Applicant: Novozymes A/S, Bagsvaerd (DK)

(72) Inventors: Lone Carstensen, Allerod (DK);
Nikolaj Spodsberg, Holte (DK);
Morten Gjermansen, Greve (DK);
Jesper Salomon, Holte (DK); Kristian Bertel Roemer M. Krogh, Holte (DK);
Eduardo Antonio Della Pia, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/301,528

(22) PCT Filed: May 24, 2017

(86) PCT No.: PCT/EP2017/062652
§ 371 (c)(1),
(2) Date: Nov. 14, 2018

(87) PCT Pub. No.: WO2017/202979
PCT Pub. Date: Nov. 30, 2017

(65) Prior Publication Data
US 2019/0289880 A1    Sep. 26, 2019

(30) Foreign Application Priority Data

May 24, 2016   (EP) ..................... 16170961

(51) Int. Cl.

| | |
|---|---|
| *A61K 35/14* | (2015.01) |
| *A23K 20/189* | (2016.01) |
| *A23K 20/174* | (2016.01) |
| *A23K 20/22* | (2016.01) |
| *A23K 20/24* | (2016.01) |
| *A23K 20/20* | (2016.01) |
| *A23K 40/10* | (2016.01) |
| *A23K 10/30* | (2016.01) |
| *C12N 9/40* | (2006.01) |

(52) U.S. Cl.
CPC ............ *A23K 20/189* (2016.05); *A23K 10/30* (2016.05); *A23K 20/174* (2016.05); *A23K 20/22* (2016.05); *A23K 20/24* (2016.05); *A23K 20/30* (2016.05); *A23K 40/10* (2016.05); *C12N 9/2465* (2013.01); *C12Y 302/01022* (2013.01)

(58) Field of Classification Search
None
See application file for complete search history.

(56) References Cited

U.S. PATENT DOCUMENTS

| | | | |
|---|---|---|---|
| 6,197,566 B1 | 3/2001 | Knap | |
| 2015/0307562 A1* | 10/2015 | Basu | ............... A61K 38/16 530/350 |
| 2016/0339078 A1* | 11/2016 | Hamill | ............... A61K 38/16 |

FOREIGN PATENT DOCUMENTS

| | | |
|---|---|---|
| CN | 1457208 A | 6/2009 |
| CN | 104805101 | 7/2015 |
| EP | 2272964 A2 | 1/2011 |
| EP | 2052078 B1 | 4/2013 |
| WO | 2009/108941 A2 | 9/2009 |

OTHER PUBLICATIONS

Zhu J. et al. (AC#A0A0F7TK13, Submitted (Nov. 2014) to the EMBL/GenBank/DDBJ database.*
Walkelin et al. (Canadian Science Publishing, 2021, pp. 1-3).*
Cao et al., J. Microbiol. Biotechnol., vol. 19, No. 11, pp. 1295-1300 (2009).
Cao et al., Genbank Accession No. FJ159431 (2011).
Daniell, Geneseq Accession No. AXR38489 (2009).
Dastager et al., ENA Accession No. KSU82091 (2015).
Dastager et al., UniProt Accession No. A0A0V8J599 (2016).
Katrolia et al., Critical Reviews in Biotechnology, vol. 34, No. 4, pp. 307-317 (2014).
Li et al., Letters in Applied Microbioly, vol. 25, No. 1, pp. 1-4 (1997).
Liu et al., UniProt Accession No. A0A0M4FME9 (2015).
Anonymous, Alignment of the FASTA Sequence of UniProtKB Entry A0A0F7TK13 and SEQ ID No. 3 (2016).

* cited by examiner

*Primary Examiner* — Hope A Robinson
(74) *Attorney, Agent, or Firm* — Elias Lambiris

(57) ABSTRACT

The present invention relates to methods of releasing galactose from legumes using polypeptides having alpha-galactosidase activity. The invention also relates to polypeptides having alpha-galactosidase activity, polynucleotides encoding the polypeptides, nucleic acid constructs, vectors, and host cells comprising the polynucleotides as well as methods of 5 producing the polypeptides. The invention also relates to compositions comprising the polypeptides of the invention and the use of the polypeptides in animal feed.

17 Claims, No Drawings
Specification includes a Sequence Listing.

SEQUENCE LISTING

```
<160> NUMBER OF SEQ ID NOS: 4

<210> SEQ ID NO 1
<211> LENGTH: 2364
<212> TYPE: DNA
<213> ORGANISM: Penicillium pseudopulvillorum
<220> FEATURE:
<221> NAME/KEY: CDS
<222> LOCATION: (1)..(82)
<220> FEATURE:
<221> NAME/KEY: sig_peptide
<222> LOCATION: (1)..(63)
<220> FEATURE:
<221> NAME/KEY: mat_peptide
<222> LOCATION: (64)..(2361)
<220> FEATURE:
<221> NAME/KEY: CDS
<222> LOCATION: (143)..(746)
<220> FEATURE:
<221> NAME/KEY: CDS
<222> LOCATION: (822)..(2361)

<400> SEQUENCE: 1 atg cag aaa gcg gtt gcg agc gct agc ttg cta gcc ctg ctc ggc tcc      48
Met Gln Lys Ala Val Ala Ser Ala Ser Leu Leu Ala Leu Leu Gly Ser
    -20                 -15                 -10 acg tcg gca gtg gca gct caa agc ttt tcc aat g gtcagttgcc            92
Thr Ser Ala Val Ala Ala Gln Ser Phe Ser Asn
 -5              -1  1               5 cttcttgagt actcttactg atccgcatac tcatactcat tcttcagcag tc  gtt     147
                                                         Val Val gtg gat ggc acc acc ttc gca ctg aac ggt gac aat ttc tcc tac cgt    195
Val Asp Gly Thr Thr Phe Ala Leu Asn Gly Asp Asn Phe Ser Tyr Arg
        10                  15                  20 ttt cat gtc gat aac gag act ggc gat ctt tgg tca gac cac ttc ggt    243
Phe His Val Asp Asn Glu Thr Gly Asp Leu Trp Ser Asp His Phe Gly
 25                  30                  35                  40 gcg agc gtg aca ggc gat ata cct ttt gag aat gtt cct gcc gtc aat    291
Ala Ser Val Thr Gly Asp Ile Pro Phe Glu Asn Val Pro Ala Val Asn
                    45                  50                  55 ggc tgg gtc ggc atg cca ggc cgt gtc cgt cga gaa ttt cct gac cag    339
Gly Trp Val Gly Met Pro Gly Arg Val Arg Arg Glu Phe Pro Asp Gln
                60                  65                  70 ggc cgg ggt gac ttc cgt att cct gcc att cgt att cga cag tcc gag    387
Gly Arg Gly Asp Phe Arg Ile Pro Ala Ile Arg Ile Arg Gln Ser Glu
            75                  80                  85 ggc tat aca gtc tcc gac ttg cag tat caa tcg tac gat gtg atc caa    435
Gly Tyr Thr Val Ser Asp Leu Gln Tyr Gln Ser Tyr Asp Val Ile Gln
        90                  95                 100 ggc aag cct gaa ctg cca gga ctg ccc gct act ttt ggt acc gat aag    483
Gly Lys Pro Glu Leu Pro Gly Leu Pro Ala Thr Phe Gly Thr Asp Lys
105                 110                 115                 120 gat gtg aca acc ttg gtc gtc cac ctt tat gat aat tat agt gcc gtg    531
Asp Val Thr Thr Leu Val Val His Leu Tyr Asp Asn Tyr Ser Ala Val
                    125                 130                 135 gca gcg gat ttg tcg tat tcc gta ttc ccc aaa tac gat gcg att gtc    579
Ala Ala Asp Leu Ser Tyr Ser Val Phe Pro Lys Tyr Asp Ala Ile Val
```

```
               140                 145                 150
cgc agt gtg aat gtt acc aac aaa ggc cag gac aac att act att gaa      627
Arg Ser Val Asn Val Thr Asn Lys Gly Gln Asp Asn Ile Thr Ile Glu
        155                 160                 165 gcg ctg gct agt ttg agt gtc gac ttt ccc tat caa gac ttg gac atg      675
Ala Leu Ala Ser Leu Ser Val Asp Phe Pro Tyr Gln Asp Leu Asp Met
170                 175                 180 atc agc ttg agg ggt gat tgg gcc cgg gaa gct cac cgc gag cga aga      723
Ile Ser Leu Arg Gly Asp Trp Ala Arg Glu Ala His Arg Glu Arg Arg
185                 190                 195                 200 aaa gtc gag tac gga ata caa gg  gtaagcctaa catacaccca cagtgatcta     776
Lys Val Glu Tyr Gly Ile Gln Gly
            205 cagcgttgag ggagaactga catacgattg ttgtcttggg attag a ttt ggc agc      831
                                                  Phe Gly Ser
                                                          210 tct acg gga tac tca tca cac ctc cac aac cca ttc ctt gct ctt gtc      879
Ser Thr Gly Tyr Ser Ser His Leu His Asn Pro Phe Leu Ala Leu Val
            215                 220                 225 gat cca agt gcc aca gaa tcc agt ggc gaa gcg tgg ggc ttc tcg tta      927
Asp Pro Ser Ala Thr Glu Ser Ser Gly Glu Ala Trp Gly Phe Ser Leu
230                 235                 240 gtg tat acc ggt tca ttt tcg gtg gac gtc gag aaa ggc tct cag ggc      975
Val Tyr Thr Gly Ser Phe Ser Val Asp Val Glu Lys Gly Ser Gln Gly
245                 250                 255 ttc act cgt gct cta ctt gga ctc aat ccc aac cag ctc tct tgg aac     1023
Phe Thr Arg Ala Leu Leu Gly Leu Asn Pro Asn Gln Leu Ser Trp Asn
260                 265                 270                 275 ctc ggt acc ggc gaa acg ata acc acg cct gaa tgc gtg tcg gtc tat     1071
Leu Gly Thr Gly Glu Thr Ile Thr Thr Pro Glu Cys Val Ser Val Tyr
            280                 285                 290 tcc cag aat gga gtc ggt ggg atg tct cgt ttg ttc cac ggg ctt tac     1119
Ser Gln Asn Gly Val Gly Gly Met Ser Arg Leu Phe His Gly Leu Tyr
            295                 300                 305 cgc aac cat ctc atc aag agc aaa ttc gcc atg aag gat cgc ccg gtc     1167
Arg Asn His Leu Ile Lys Ser Lys Phe Ala Met Lys Asp Arg Pro Val
            310                 315                 320 cta ttg aac agc tgg gag ggc cta ggt ttt gac tac aat gag agc acc     1215
Leu Leu Asn Ser Trp Glu Gly Leu Gly Phe Asp Tyr Asn Glu Ser Thr
325                 330                 335 atc tac aac ctt gct caa gaa tct gca gac ttg gga gtc aaa ctc ttc     1263
Ile Tyr Asn Leu Ala Gln Glu Ser Ala Asp Leu Gly Val Lys Leu Phe
340                 345                 350                 355 gtc ctg gat gat gga tgg ttc ggt gat aag tat cct cga ctg tct gac     1311
Val Leu Asp Asp Gly Trp Phe Gly Asp Lys Tyr Pro Arg Leu Ser Asp
            360                 365                 370 aac gcc ggt tta ggt gac tgg gta ccc aat ccc gac agg ttc cca gac     1359
Asn Ala Gly Leu Gly Asp Trp Val Pro Asn Pro Asp Arg Phe Pro Asp
            375                 380                 385 ggt ctg gat cac gca gtg act agt att acg gcg ctg aaa gct gcg aac     1407
Gly Leu Asp His Ala Val Thr Ser Ile Thr Ala Leu Lys Ala Ala Asn
            390                 395                 400 aca tcc acc aag ctc cga ttt ggt ctc tgg ttt gag cct gag atg gtc     1455
Thr Ser Thr Lys Leu Arg Phe Gly Leu Trp Phe Glu Pro Glu Met Val
            405                 410                 415 aac cct aat tcc agc ctc tat cac gaa cac cct gac tgg gcc tta cat     1503
Asn Pro Asn Ser Ser Leu Tyr His Glu His Pro Asp Trp Ala Leu His
420                 425                 430                 435 gcc gga tcc tat cca cgc aca gaa cga cgt aat cag ctc gtt tta aac     1551
```

```
Ala Gly Ser Tyr Pro Arg Thr Glu Arg Arg Asn Gln Leu Val Leu Asn
                440                 445                 450 gtg gct ctt cca gag gta caa gac ttt atc atc aag tct gtg tct agt      1599
Val Ala Leu Pro Glu Val Gln Asp Phe Ile Ile Lys Ser Val Ser Ser
            455                 460                 465 att ctg agc agc gcc gat atc acc tat gtg aag tgg gat aac aat cgt      1647
Ile Leu Ser Ser Ala Asp Ile Thr Tyr Val Lys Trp Asp Asn Asn Arg
        470                 475                 480 ggt att cat gaa atg ccc tcg cca tcc act gac cac gaa tac atg cta      1695
Gly Ile His Glu Met Pro Ser Pro Ser Thr Asp His Glu Tyr Met Leu
    485                 490                 495 ggc atg tac cgg gta ttc aac aac ttg acc act caa ttc cct aat gtt      1743
Gly Met Tyr Arg Val Phe Asn Asn Leu Thr Thr Gln Phe Pro Asn Val
500                 505                 510                 515 ctg tgg gag ggc tgc gct tca ggt ggc ggt cgc ttc gat gct ggt gta      1791
Leu Trp Glu Gly Cys Ala Ser Gly Gly Gly Arg Phe Asp Ala Gly Val
                520                 525                 530 ctc cag tac ttc ccc cag atc tgg acc tct gat gat acc gat gcc gtt      1839
Leu Gln Tyr Phe Pro Gln Ile Trp Thr Ser Asp Asp Thr Asp Ala Val
            535                 540                 545 gag cgc atc acc att caa atg gga acc tca ctc gtg tat ccc ccg agc      1887
Glu Arg Ile Thr Ile Gln Met Gly Thr Ser Leu Val Tyr Pro Pro Ser
        550                 555                 560 gcg atg ggt gct cac ctt tct gcc gtc ccc aac caa cag acc ggt agg      1935
Ala Met Gly Ala His Leu Ser Ala Val Pro Asn Gln Gln Thr Gly Arg
    565                 570                 575 aca ctg cct gtc gca ttc cgt ggc cac gtt gcc atg atg gga ggc tct      1983
Thr Leu Pro Val Ala Phe Arg Gly His Val Ala Met Met Gly Gly Ser
580                 585                 590                 595 ttc ggc ctt gag cta gat ccc gcc gaa atc ccg agt gat gac aag gct      2031
Phe Gly Leu Glu Leu Asp Pro Ala Glu Ile Pro Ser Asp Asp Lys Ala
                600                 605                 610 gct ctg cct ggc ctc att tca ctt gct gag aag gtc aac cca atc atc      2079
Ala Leu Pro Gly Leu Ile Ser Leu Ala Glu Lys Val Asn Pro Ile Ile
            615                 620                 625 ttg acc ggg gat atg tac cgc ttg aat cta ccg gag gac tcg aat tgg      2127
Leu Thr Gly Asp Met Tyr Arg Leu Asn Leu Pro Glu Asp Ser Asn Trp
        630                 635                 640 ccc gcc gtt caa ttt atc tcg caa gat gcg tcg cag gcg gtg cta ttc      2175
Pro Ala Val Gln Phe Ile Ser Gln Asp Ala Ser Gln Ala Val Leu Phe
    645                 650                 655 tac ttc cag att aac ccc aac atc aat cat gca cta ccg tgg atc aag      2223
Tyr Phe Gln Ile Asn Pro Asn Ile Asn His Ala Leu Pro Trp Ile Lys
660                 665                 670                 675 ctg caa gga ttg gat ccc aag gca gtc tat agc gtg gat ggt aat gcc      2271
Leu Gln Gly Leu Asp Pro Lys Ala Val Tyr Ser Val Asp Gly Asn Ala
                680                 685                 690 acg tat tca gga tca gcc ctg atg aat gtt ggg tta cag ttt gtc ttt      2319
Thr Tyr Ser Gly Ser Ala Leu Met Asn Val Gly Leu Gln Phe Val Phe
            695                 700                 705 gaa aca gac tac ggc agt caa gtt gtg ttc att gag aag cag tga           2364
Glu Thr Asp Tyr Gly Ser Gln Val Val Phe Ile Glu Lys Gln
        710                 715                 720

<210> SEQ ID NO 2
<211> LENGTH: 742
<212> TYPE: PRT
<213> ORGANISM: Penicillium pseudopulvillorum

<400> SEQUENCE: 2
```

```
Met Gln Lys Ala Val Ala Ser Ala Ser Leu Leu Ala Leu Leu Gly Ser
-20                 -15                 -10

Thr Ser Ala Val Ala Ala Gln Ser Phe Ser Asn Val Val Asp Gly
 -5              -1   1           5                   10

Thr Thr Phe Ala Leu Asn Gly Asp Asn Phe Ser Tyr Arg Phe His Val
            15                  20                  25

Asp Asn Glu Thr Gly Asp Leu Trp Ser Asp His Phe Gly Ala Ser Val
        30                  35                  40

Thr Gly Asp Ile Pro Phe Glu Asn Val Pro Ala Val Asn Gly Trp Val
    45                  50                  55

Gly Met Pro Gly Arg Val Arg Arg Glu Phe Pro Asp Gln Gly Arg Gly
60                  65                  70                  75

Asp Phe Arg Ile Pro Ala Ile Arg Ile Arg Gln Ser Glu Gly Tyr Thr
                80                  85                  90

Val Ser Asp Leu Gln Tyr Gln Ser Tyr Asp Val Ile Gln Gly Lys Pro
            95                  100                 105

Glu Leu Pro Gly Leu Pro Ala Thr Phe Gly Thr Asp Lys Asp Val Thr
        110                 115                 120

Thr Leu Val Val His Leu Tyr Asp Asn Tyr Ser Ala Val Ala Ala Asp
    125                 130                 135

Leu Ser Tyr Ser Val Phe Pro Lys Tyr Asp Ala Ile Val Arg Ser Val
140                 145                 150                 155

Asn Val Thr Asn Lys Gly Gln Asp Asn Ile Thr Ile Glu Ala Leu Ala
                160                 165                 170

Ser Leu Ser Val Asp Phe Pro Tyr Gln Asp Leu Asp Met Ile Ser Leu
            175                 180                 185

Arg Gly Asp Trp Ala Arg Glu Ala His Arg Glu Arg Lys Val Glu
    190                 195                 200

Tyr Gly Ile Gln Gly Phe Gly Ser Ser Thr Gly Tyr Ser Ser His Leu
    205                 210                 215

His Asn Pro Phe Leu Ala Leu Val Asp Pro Ser Ala Thr Glu Ser Ser
220                 225                 230                 235

Gly Glu Ala Trp Gly Phe Ser Leu Val Tyr Thr Gly Ser Phe Ser Val
                240                 245                 250

Asp Val Glu Lys Gly Ser Gln Gly Phe Thr Arg Ala Leu Leu Gly Leu
            255                 260                 265

Asn Pro Asn Gln Leu Ser Trp Asn Leu Gly Thr Gly Glu Thr Ile Thr
    270                 275                 280

Thr Pro Glu Cys Val Ser Val Tyr Ser Gln Asn Gly Val Gly Gly Met
    285                 290                 295

Ser Arg Leu Phe His Gly Leu Tyr Arg Asn His Leu Ile Lys Ser Lys
300                 305                 310                 315

Phe Ala Met Lys Asp Arg Pro Val Leu Leu Asn Ser Trp Glu Gly Leu
                320                 325                 330

Gly Phe Asp Tyr Asn Glu Ser Thr Ile Tyr Asn Leu Ala Gln Glu Ser
            335                 340                 345

Ala Asp Leu Gly Val Lys Leu Phe Val Leu Asp Asp Gly Trp Phe Gly
        350                 355                 360

Asp Lys Tyr Pro Arg Leu Ser Asp Asn Ala Gly Leu Gly Asp Trp Val
    365                 370                 375

Pro Asn Pro Asp Arg Phe Pro Asp Gly Leu Asp His Ala Val Thr Ser
380                 385                 390                 395

Ile Thr Ala Leu Lys Ala Ala Asn Thr Ser Thr Lys Leu Arg Phe Gly
```

```
            400             405             410
Leu Trp Phe Glu Pro Glu Met Val Asn Pro Asn Ser Leu Tyr His
            415             420             425

Glu His Pro Asp Trp Ala Leu His Ala Gly Ser Tyr Pro Arg Thr Glu
            430             435             440

Arg Arg Asn Gln Leu Val Leu Asn Val Ala Leu Pro Glu Val Gln Asp
            445             450             455

Phe Ile Ile Lys Ser Val Ser Ser Ile Leu Ser Ser Ala Asp Ile Thr
460             465             470             475

Tyr Val Lys Trp Asp Asn Asn Arg Gly Ile His Glu Met Pro Ser Pro
                480             485             490

Ser Thr Asp His Glu Tyr Met Leu Gly Met Tyr Arg Val Phe Asn Asn
            495             500             505

Leu Thr Thr Gln Phe Pro Asn Val Leu Trp Glu Gly Cys Ala Ser Gly
            510             515             520

Gly Gly Arg Phe Asp Ala Gly Val Leu Gln Tyr Phe Pro Gln Ile Trp
            525             530             535

Thr Ser Asp Asp Thr Asp Ala Val Glu Arg Ile Thr Ile Gln Met Gly
540             545             550             555

Thr Ser Leu Val Tyr Pro Pro Ser Ala Met Gly Ala His Leu Ser Ala
                560             565             570

Val Pro Asn Gln Gln Thr Gly Arg Thr Leu Pro Val Ala Phe Arg Gly
            575             580             585

His Val Ala Met Met Gly Gly Ser Phe Gly Leu Glu Leu Asp Pro Ala
            590             595             600

Glu Ile Pro Ser Asp Asp Lys Ala Ala Leu Pro Gly Leu Ile Ser Leu
            605             610             615

Ala Glu Lys Val Asn Pro Ile Ile Leu Thr Gly Asp Met Tyr Arg Leu
620             625             630             635

Asn Leu Pro Glu Asp Ser Asn Trp Pro Ala Val Gln Phe Ile Ser Gln
                640             645             650

Asp Ala Ser Gln Ala Val Leu Phe Tyr Phe Gln Ile Asn Pro Asn Ile
            655             660             665

Asn His Ala Leu Pro Trp Ile Lys Leu Gln Gly Leu Asp Pro Lys Ala
            670             675             680

Val Tyr Ser Val Asp Gly Asn Ala Thr Tyr Ser Gly Ser Ala Leu Met
            685             690             695

Asn Val Gly Leu Gln Phe Val Phe Glu Thr Asp Tyr Gly Ser Gln Val
700             705             710             715

Val Phe Ile Glu Lys Gln
                720

<210> SEQ ID NO 3
<211> LENGTH: 721
<212> TYPE: PRT
<213> ORGANISM: Penicillium pseudopulvillorum
<220> FEATURE:
<221> NAME/KEY: mat_peptide
<222> LOCATION: (1)..(721)

<400> SEQUENCE: 3

Ala Gln Ser Phe Ser Asn Val Val Asp Gly Thr Thr Phe Ala Leu
1               5                   10                  15

Asn Gly Asp Asn Phe Ser Tyr Arg Phe His Val Asp Asn Glu Thr Gly
                20                  25                  30
```

```
Asp Leu Trp Ser Asp His Phe Gly Ala Ser Val Thr Gly Asp Ile Pro
         35                  40                  45

Phe Glu Asn Val Pro Ala Val Asn Gly Trp Val Gly Met Pro Gly Arg
 50                  55                  60

Val Arg Arg Glu Phe Pro Asp Gln Gly Arg Gly Asp Phe Arg Ile Pro
 65                  70                  75                  80

Ala Ile Arg Ile Arg Gln Ser Glu Gly Tyr Thr Val Ser Asp Leu Gln
                 85                  90                  95

Tyr Gln Ser Tyr Asp Val Ile Gln Gly Lys Pro Glu Leu Pro Gly Leu
                100                 105                 110

Pro Ala Thr Phe Gly Thr Asp Lys Asp Val Thr Thr Leu Val Val His
                115                 120                 125

Leu Tyr Asp Asn Tyr Ser Ala Val Ala Asp Leu Ser Tyr Ser Val
130                 135                 140

Phe Pro Lys Tyr Asp Ala Ile Val Arg Ser Val Asn Val Thr Asn Lys
145                 150                 155                 160

Gly Gln Asp Asn Ile Thr Ile Glu Ala Leu Ala Ser Leu Ser Val Asp
                165                 170                 175

Phe Pro Tyr Gln Asp Leu Asp Met Ile Ser Leu Arg Gly Asp Trp Ala
                180                 185                 190

Arg Glu Ala His Arg Glu Arg Lys Val Glu Tyr Gly Ile Gln Gly
                195                 200                 205

Phe Gly Ser Ser Thr Gly Tyr Ser Ser His Leu His Asn Pro Phe Leu
210                 215                 220

Ala Leu Val Asp Pro Ser Ala Thr Glu Ser Ser Gly Glu Ala Trp Gly
225                 230                 235                 240

Phe Ser Leu Val Tyr Thr Gly Ser Phe Ser Val Asp Val Glu Lys Gly
                245                 250                 255

Ser Gln Gly Phe Thr Arg Ala Leu Leu Gly Leu Asn Pro Asn Gln Leu
                260                 265                 270

Ser Trp Asn Leu Gly Thr Gly Glu Thr Ile Thr Thr Pro Glu Cys Val
                275                 280                 285

Ser Val Tyr Ser Gln Asn Gly Val Gly Gly Met Ser Arg Leu Phe His
290                 295                 300

Gly Leu Tyr Arg Asn His Leu Ile Lys Ser Lys Phe Ala Met Lys Asp
305                 310                 315                 320

Arg Pro Val Leu Leu Asn Ser Trp Glu Gly Leu Gly Phe Asp Tyr Asn
                325                 330                 335

Glu Ser Thr Ile Tyr Asn Leu Ala Gln Glu Ser Ala Asp Leu Gly Val
                340                 345                 350

Lys Leu Phe Val Leu Asp Asp Gly Trp Phe Gly Asp Lys Tyr Pro Arg
                355                 360                 365

Leu Ser Asp Asn Ala Gly Leu Gly Asp Trp Val Pro Asn Pro Asp Arg
                370                 375                 380

Phe Pro Asp Gly Leu Asp His Ala Val Thr Ser Ile Thr Ala Leu Lys
385                 390                 395                 400

Ala Ala Asn Thr Ser Thr Lys Leu Arg Phe Gly Leu Trp Phe Glu Pro
                405                 410                 415

Glu Met Val Asn Pro Asn Ser Ser Leu Tyr His Glu His Pro Asp Trp
                420                 425                 430

Ala Leu His Ala Gly Ser Tyr Pro Arg Thr Glu Arg Arg Asn Gln Leu
                435                 440                 445

Val Leu Asn Val Ala Leu Pro Glu Val Gln Asp Phe Ile Ile Lys Ser
```

```
            450                 455                 460
Val Ser Ser Ile Leu Ser Ser Ala Asp Ile Thr Tyr Val Lys Trp Asp
465                 470                 475                 480

Asn Asn Arg Gly Ile His Glu Met Pro Ser Pro Ser Thr Asp His Glu
                485                 490                 495

Tyr Met Leu Gly Met Tyr Arg Val Phe Asn Asn Leu Thr Thr Gln Phe
            500                 505                 510

Pro Asn Val Leu Trp Glu Gly Cys Ala Ser Gly Gly Arg Phe Asp
        515                 520                 525

Ala Gly Val Leu Gln Tyr Phe Pro Gln Ile Trp Thr Ser Asp Thr
    530                 535                 540

Asp Ala Val Glu Arg Ile Thr Ile Gln Met Gly Thr Ser Leu Val Tyr
545                 550                 555                 560

Pro Pro Ser Ala Met Gly Ala His Leu Ser Ala Val Pro Asn Gln Gln
                565                 570                 575

Thr Gly Arg Thr Leu Pro Val Ala Phe Arg Gly His Val Ala Met Met
            580                 585                 590

Gly Gly Ser Phe Gly Leu Glu Leu Asp Pro Ala Glu Ile Pro Ser Asp
        595                 600                 605

Asp Lys Ala Ala Leu Pro Gly Leu Ile Ser Leu Ala Glu Lys Val Asn
    610                 615                 620

Pro Ile Ile Leu Thr Gly Asp Met Tyr Arg Leu Asn Leu Pro Glu Asp
625                 630                 635                 640

Ser Asn Trp Pro Ala Val Gln Phe Ile Ser Gln Asp Ala Ser Gln Ala
                645                 650                 655

Val Leu Phe Tyr Phe Gln Ile Asn Pro Asn Ile Asn His Ala Leu Pro
            660                 665                 670

Trp Ile Lys Leu Gln Gly Leu Asp Pro Lys Ala Val Tyr Ser Val Asp
        675                 680                 685

Gly Asn Ala Thr Tyr Ser Gly Ser Ala Leu Met Asn Val Gly Leu Gln
    690                 695                 700

Phe Val Phe Glu Thr Asp Tyr Gly Ser Gln Val Val Phe Ile Glu Lys
705                 710                 715                 720

Gln

<210> SEQ ID NO 4
<211> LENGTH: 747
<212> TYPE: PRT
<213> ORGANISM: Aspergillus niger

<400> SEQUENCE: 4

Met Ile Gly Ser Ser His Ala Val Val Ala Leu Gly Leu Phe Thr Leu
1               5                   10                  15

Tyr Gly His Ser Ala Ala Ala Pro Ala Thr Gly Ala Ser Asn Ser Gln
            20                  25                  30

Thr Ile Val Thr Asn Gly Thr Ser Phe Ala Leu Asn Gly Asp Asn Val
        35                  40                  45

Ser Tyr Arg Phe His Val Asn Ser Thr Thr Gly Asp Leu Ile Ser Asp
    50                  55                  60

His Phe Gly Gly Val Val Ser Gly Thr Ile Pro Ser Pro Val Glu Pro
65                  70                  75                  80

Ala Val Asn Gly Trp Val Gly Met Pro Gly Arg Ile Arg Arg Glu Phe
                85                  90                  95

Pro Asp Gln Gly Arg Gly Asp Phe Arg Ile Pro Ala Val Arg Ile Arg
```

```
            100                 105                 110
Glu Ser Ala Gly Tyr Thr Val Ser Asp Leu Gln Tyr Val Ser His Glu
            115                 120                 125
Val Ile Glu Gly Lys Asn Ala Leu Pro Gly Leu Pro Ala Thr Phe Gly
            130                 135                 140
Asp Ala Gln Ala Val Thr Thr Leu Val Val His Leu Tyr Asp Asn Tyr
145                 150                 155                 160
Ser Ser Val Ala Ala Asp Leu Ser Tyr Ser Ile Phe Pro Lys Tyr Asp
            165                 170                 175
Ala Ile Val Arg Ser Val Asn Val Ile Asn Gln Gly Pro Gly Asn Ile
            180                 185                 190
Thr Ile Glu Ala Leu Ala Ser Ile Ser Ile Asp Phe Pro Tyr Glu Asp
            195                 200                 205
Leu Asp Met Val Ser Leu Arg Gly Asp Trp Ala Arg Glu Ala Asn Val
210                 215                 220
Gln Arg Ser Lys Val Gln Tyr Gly Val Gln Gly Phe Gly Ser Ser Thr
225                 230                 235                 240
Gly Tyr Ser Ser His Leu His Asn Pro Phe Leu Ala Ile Val Asp Pro
            245                 250                 255
Ala Thr Thr Glu Ser Gln Gly Glu Ala Trp Gly Phe Asn Leu Val Tyr
            260                 265                 270
Thr Gly Ser Phe Ser Ala Gln Val Glu Lys Gly Ser Gln Gly Phe Thr
            275                 280                 285
Arg Ala Leu Leu Gly Phe Asn Pro Asp Gln Leu Ser Trp Asn Leu Gly
            290                 295                 300
Pro Gly Glu Thr Leu Thr Ser Pro Glu Cys Val Ala Val Tyr Ser Asp
305                 310                 315                 320
Lys Gly Leu Gly Ser Val Ser Arg Lys Phe His Arg Leu Tyr Arg Asn
            325                 330                 335
His Leu Met Lys Ser Lys Phe Ala Thr Ser Asp Arg Pro Val Leu Leu
            340                 345                 350
Asn Ser Trp Glu Gly Val Tyr Phe Asp Tyr Asn Gln Ser Ser Ile Glu
            355                 360                 365
Thr Leu Ala Glu Glu Ser Ala Ala Leu Gly Val His Leu Phe Val Met
            370                 375                 380
Asp Asp Gly Trp Phe Gly Asp Lys Tyr Pro Arg Val Ser Asp Asn Ala
385                 390                 395                 400
Gly Leu Gly Asp Trp Met Pro Asn Pro Ala Arg Phe Pro Asp Gly Leu
            405                 410                 415
Thr Pro Val Val Gln Asp Ile Thr Asn Leu Thr Val Asn Gly Thr Glu
            420                 425                 430
Ser Thr Lys Leu Arg Phe Gly Ile Trp Val Glu Pro Glu Met Val Asn
            435                 440                 445
Pro Asn Ser Thr Leu Tyr His Glu His Pro Glu Trp Ala Leu His Ala
450                 455                 460
Gly Pro Tyr Pro Arg Thr Glu Arg Arg Asn Gln Leu Val Leu Asn Leu
465                 470                 475                 480
Ala Leu Pro Ala Val Gln Asp Phe Ile Ile Asp Phe Met Thr Asn Leu
            485                 490                 495
Leu Gln Asp Thr Gly Ile Ser Tyr Val Lys Trp Asp Asn Asn Arg Gly
            500                 505                 510
Ile His Glu Thr Pro Ser Pro Ser Thr Asp His Gln Tyr Met Leu Gly
            515                 520                 525
```

-continued

```
Leu Tyr Arg Val Phe Asp Thr Leu Thr Thr Arg Phe Pro Asp Val Leu
            530                 535                 540

Trp Glu Gly Cys Ala Ser Gly Gly Gly Arg Phe Asp Ala Gly Met Leu
545                 550                 555                 560

Gln Tyr Val Pro Gln Ile Trp Thr Ser Asp Asn Thr Asp Ala Ile Asp
            565                 570                 575

Arg Ile Thr Ile Gln Phe Gly Thr Ser Leu Ala Tyr Pro Pro Ser Ala
            580                 585                 590

Met Gly Ala His Leu Ser Ala Val Pro Asn Ala Gln Thr Gly Arg Thr
            595                 600                 605

Val Pro Ile Thr Phe Arg Ala His Val Ala Met Met Gly Gly Ser Phe
            610                 615                 620

Gly Leu Glu Leu Asp Pro Ala Thr Val Glu Gly Asp Glu Ile Val Pro
625                 630                 635                 640

Glu Leu Leu Ala Leu Ala Glu Lys Val Asn Pro Ile Ile Leu Asn Gly
            645                 650                 655

Asp Leu Tyr Arg Leu Arg Leu Pro Gln Asp Ser Gln Trp Pro Ala Ala
            660                 665                 670

Leu Phe Val Thr Gln Asp Gly Ala Gln Ala Val Leu Phe Tyr Phe Gln
            675                 680                 685

Val Gln Pro Asn Val Asn His Ala Val Pro Trp Val Arg Leu Gln Gly
            690                 695                 700

Leu Asp Pro Lys Ala Asp Tyr Thr Val Asp Gly Asp Gln Thr Tyr Ser
705                 710                 715                 720

Gly Ala Thr Leu Met Asn Leu Gly Leu Gln Tyr Ser Phe Asp Thr Glu
            725                 730                 735

Tyr Gly Ser Lys Val Val Phe Leu Glu Arg Gln
            740                 745
```

ANIMAL FEED ADDITIVES

CROSS-REFERENCE TO RELATED APPLICATIONS

This application is a 35 U.S.C. 371 national application of international application no. PCT/EP2017/062652 filed May 24, 2017 which claims priority or the benefit under 35 U.S.C. 119 of European application no. 16170961.3 filed May 24, 2018, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods of releasing galactose from legumes using polypeptides having alpha-galactosidase activity. The invention also relates to polypeptides having alpha-galactosidase activity, polynucleotides encoding the polypeptides, nucleic acid constructs, vectors, and host cells comprising the polynucleotides as well as methods of producing the polypeptides. The invention also relates to compositions comprising the polypeptides of the invention and the use of the polypeptides in animal feed.

Description of the Related Art

Soybean is a species of legume native to East Asia and is the second biggest animal feed crop globally and the biggest feed protein source. Soy bean can be manufactured (defatted) to produce soybean meal (SBM), and SBM is a significant and cheap source of protein for animal feeds. Other common types of legume are chickpea, lupin, lentil, peanut, beans or peas which can also be processed and used as animal feed.

Alpha-galactosidase is a glycoside hydrolase enzyme that hydrolyses the terminal alpha-galactosyl moieties from glycolipids and glycoproteins that is present in, e.g. legumes, vegetables, grains, cereals and the like. Alpha-galactosidases are produced by various microorganisms, plants and animals, but monogastric animals are deficient in intestinal alpha-galactosidase production and consequently are incapable of decomposing ingested alpha-galactosidases by themselves. Instead, ingested alpha-galactosidases are decomposed by microorganisms present in the large intestines, where this microbial fermentation may cause flatulence and possibly wet litter.

Animal feed supplemented with alpha-galactosidases can help the animal digest the food thereby obtaining a higher release of galactose and sucrose which will promote animal growth (performance). However, the alpha-galactoside needs to survive passage through the stomach, i.e. low pH and proteases such as pepsin, before it can get to work in the intestine. Animal feed, especially for poultry, is normally pelleted before being fed and the enzyme also needs to survive the pelleting conditions. Thus the object of this invention is to provide acid stable alpha-galactosidases which are highly effective at releasing galactose and sucrose from legumes.

SUMMARY OF THE INVENTION

The present invention relates to an animal feed additive, granules and liquid formulations comprising one or more GH36 polypeptides having alpha-galactosidase activity selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;

(b) a polypeptide encoded by a polynucleotide that hybridizes under high stringency conditions, or very high stringency conditions with
  (i) the mature polypeptide coding sequence of SEQ ID NO: 1,
  (ii) the cDNA sequence thereof, or
  (iii) the full-length complementary strand of (i) or (ii);

(c) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;

(d) a variant of the polypeptide selected from the group consisting of SEQ ID NO: 3, wherein the variant has alpha-galactosidase activity and comprises one or more amino acid substitutions, and/or one or more amino acid deletions, and/or one or more amino acid insertions or any combination thereof in up to 50 positions;

(e) a polypeptide comprising the polypeptide of (a), (b), (c) or (d) and a N-terminal and/or C-terminal His-tag and/or HQ-tag;

(f) a polypeptide comprising the polypeptide of (a), (b), (c) or (d) and a N-terminal and/or C-terminal extension of up to 10 amino acids, e.g. 1, 2, 3, 4, 5, 6, 7, 8, 9 or 10 amino acids; and (g) a fragment of the polypeptide of (a), (b), (c) or (d) having alpha-galactosidase activity and having at least 90% of the length of the mature polypeptide.

The invention further relates to isolated polypeptides having alpha-galactosidase activity as defined in the claims; compositions, such as animal feed, comprising the polypeptide of the invention and uses thereof; methods of releasing galactose from plant based material; methods of improving the performance of an animal; methods for improving the nutritional value of an animal feed; polynucleotides encoding the polypeptides of the present invention; nucleic acid constructs; expression vectors; recombinant host cells comprising the polynucleotides; methods of producing the polypeptides and uses thereof.

OVERVIEW OF SEQUENCE LISTING

SEQ ID NO: 1 is the cDNA sequence of GH36 alpha-galactosidase as isolated from *Penicillium pseudopulvillorum*.

SEQ ID NO: 2 is the amino acid sequence as deduced from SEQ ID NO: 2.

SEQ ID NO: 3 is the amino acid sequence of the mature GH36 alpha-galactosidase from *Penicillium pseudopulvilorum*.

SEQ ID NO: 4 is the corrected amino acid sequence of the alpha-galactosidase as disclosed in WO1994/23022.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-galactosidase: The term "alpha-galactosidase", also called α-D-galactoside galactohydrolase (E.C. 3.2.1.22), means an enzyme that catalyses the hydrolysis of terminal, non-reducing α-D-galactose residues in α-D-galactosides, such as galactose oligosaccharides, galactomannans and galactolipids. Alpha-galactosidase activity can be determined using 4-nitrophenyl α-D-galactopyranoside (available from Megazyme International, Bray, Co. Wicklow, Ireland) as substrate in 100 mM MES (Sigma) buffer pH 7.0±0.05 at room temperature. The enzyme is diluted in 2-fold dilutions and then the 4-nitrophenyl α-D-galactopyranoside substrate is dissolved in the solution containing the enzyme. The alpha-galactosidase activity is followed directly in the buffer by measuring the absorbance of released pNP at 405 nm as function of time. A detailed assay can be found in the alpha-galactosidase assay as described herein.

In one aspect, the polypeptides of the present invention have at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3.

In one aspect, the polypeptide has improved gastric stability compared to control (wherein control is defined as SEQ ID NO: 4). In an embodiment, the gastric stability is measured as the half-life at 40° C. pH3 with 0.1 mg/ml pepsin. In an embodiment, gastric stability is measured as described in example 4 herein. In a further embodiment, the polypeptide has a half-life of at least 90 minutes, such as 2 hours, 3 hours or 4 hours.

In one aspect, the polypeptide has increased alpha-galactosidase activity compared to control (wherein control is defined as SEQ ID NO: 4). In one embodiment, activity is measured using 4-nitrophenyl α-D-galactopyranoside as substrate. In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the polypeptide has an activity of at least 100000 (mOD/min)/(mg/ml), such as at least 150000, at least 200000, at least 250000, or at least 300000 (mOD/min)/(mg/ml) using 4-nitrophenyl α-D-galactopyranoside as substrate.

Animal: The term "animal" refers to all animals except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide or domain; wherein the fragment has alpha-galactosidase activity.

In one aspect, the fragment comprises at least 90% of the length of the mature polypeptide, such as at least 648 amino acids of SEQ ID NO: 2 or at least 648 amino acids of SEQ ID NO: 3. In another aspect, the fragment comprises at least 92% of the length of the mature polypeptide, such as at least 663 amino acids of SEQ ID NO: 2 or at least 663 amino acids of SEQ ID NO: 3. In another aspect, the fragment comprises at least 94% of the length of the mature polypeptide, such as at least 677 amino acids of SEQ ID NO: 2 or at least 677 amino acids of SEQ ID NO: 3.

In another aspect, the fragment comprises at least 96% of the length of the mature polypeptide, such as at least 692 amino acids of SEQ ID NO: 2 or at least 692 amino acids of SEQ ID NO: 3. In another aspect, the fragment comprises at least 98% of the length of the mature polypeptide, such as at least 706 amino acids of SEQ ID NO: 2 or at least 706 amino acids of SEQ ID NO: 3. In another aspect, the fragment comprises at least 99% of the length of the mature polypeptide, such as at least 713 amino acids of SEQ ID NO: 2 or at least 713 amino acids of SEQ ID NO: 3.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 721 of SEQ ID NO: 2. In another aspect, the mature polypeptide is amino acids 1 to 721 of SEQ ID NO: 3.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having alpha-galactosidase activity. In one aspect, the mature polypeptide coding sequence is the joined sequence of nucleotides 1 to 82, nucleotides 143 to 746 and nucleotides 822 to 2361 of SEQ ID NO: 1.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g. the small intestine. Nutrient digestibility may be measured as the difference between what is administered to the subject and what. comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Release x g galactose per kg soybean meal: The term "release x g galactose per kg soybean meal" means the amount of galactose in grams which is released into the supernatant after soybean meal has been incubation with an enzyme. For the purpose of the present invention, the release of galactose per kg soybean meal may be determined when performed under the reaction conditions 20 mg polypeptide per kg soybean meal in 10% w/v 0.1M citric acid-phosphate buffer pH 6.5 incubating at 40° C. for 2 hours as described in the galactose assay herein.

In a more detailed embodiment, a 10 w/v % slurry of soybean meal is prepared from soybean meal milled to a 0.5 mm particle size and 0.1 M citric acid-phosphate buffer, pH 6.5±0.05. The incubation vessels with the 10 w/v % slurry of soybean meal is heated to a stable temperature of 40±2° C. while stirring. When a stable temperature had been achieved, the six D-(+)-galactose standards are added to the incubation vessels to in-vessel concentrations of 5, 2.5, 1.25, 0.625, 0.313 and 0.157 mg galactose per mL incubation volume. Each standard is incubated in duplicates. The diluted enzymes are then added to their respective incubation vessels in the volumes required to reach their desired concentrations (in mg EP/kg soybean meal). Each enzyme treatment is incubated in triplicates. Additionally, two times three incubation vessels are included without standards or enzyme treatments as blank treatments to obtain the baseline galactose concentration in the soybean meal slurry. The incubation vessels are incubated at 40±2° C., while stirring for 2 hours. After incubation the vessels are centrifuged at 1500 g at 5° C. for 15 minutes. The supernatants are then analyzed in an assay based on the Raffinose/Galactose kit from Megazyme (product name K-RAFGA) and the concentration of galactose is then calculated as described in the galactose assay herein.

Plant based material: The term "plant based material" means that the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Sequence identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows:

(Identical Residues×100)/(Length of Alignment–
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the –nobrief option) is used as the percent identity and is calculated as follows:

(Identical Deoxyribonucleotides×100)/(Length of
Alignment–Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2.0×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2.0×SSC, 0.2% SDS at 65° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1.0×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1.0×SSC, 0.2% SDS at 70° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.5×SSC, 0.2% SDS at 70° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.5×SSC, 0.2% SDS at 75° C.

Subsequence: The term "subsequence" means a polynucleotide having one or more (e.g., several) nucleotides absent from the 5' and/or 3' end of a mature polypeptide coding sequence; wherein the subsequence encodes a fragment having alpha-galactosidase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having alpha-galactosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

In one aspect, the variants of the present invention have at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3 when using 4-nitrophenyl α-D-galactopyranoside as substrate as described herein.

In one aspect, the variant has improved gastric stability compared to control (wherein control is defined as SEQ ID NO: 4). In an embodiment, the gastric stability is measured as the half-life at 40° C. pH3 with 0.1 mg/ml pepsin. In an embodiment, gastric stability is measured as described in example 4 herein. In a further embodiment, the variant has a half-life of at least 90 minutes, such as 2 hours, 3 hours or 4 hours.

In one aspect, the variant has increased alpha-galactosidase activity compared to control (wherein control is defined as SEQ ID NO: 4). In one embodiment, activity is measured using 4-nitrophenyl α-D-galactopyranoside as substrate. In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the variant has an activity of at least 100000 (mOD/min)/(mg/ml), such as at least 150000, at least 200000, at least 250000, or at least 300000 (mOD/min)/(mg/ml) using 4-nitrophenyl α-D-galactopyranoside as substrate.

DETAILED DESCRIPTION OF THE INVENTION

The inventors have found that certain alpha-galactosidases from glycoside hydrolase family 36 (herein referred to as GH36) are surprisingly good at degrading the raffinose family of oligosaccharides (RFOs), such as the trisaccharide raffinose, the tetrasaccharide stachyose, and the pentasaccharide verbascose. These RFOs are typically found in plants from the taxonomic subclass rosids, specifically the subfamily Papilionoideae, such as in soy beans, chickpea, beans, lupin, lentil, peanut and peas or the tribe Brassiceae, such as in canola or rapeseed.

Efficient alpha-galactosidases are required to effectively degrade RFO's. However, the alpha-galactoside also needs to survive passage through the stomach of the animal where there is a low pH and proteases such as pepsin, before it can get to work in the intestine. If the alpha-galactosidase is degraded or denatured whilst passing through the stomach then it will not be present to work in the intestine of the animal.

The degradation of RFO's can be measured as the amount of galactose released into the supernatant when e.g. soybean meal is treated with an alpha-galactosidase. Increased amounts of solubilisation will result in more galactose being released which can be detected using e.g. the Galactose SBM Assay method as described herein. Thus the invention relates to an acid stable alpha-galactosidase which is also highly efficient at releasing galactose from plant material, such as soybean meal.

Animal Feed and Animal Feed Additives

In a first aspect, the invention relates to animal feed additives comprising one or more GH36 polypeptides having alpha-galactosidase activity, wherein the polypeptide having alpha-galactosidase activity has at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 2.

In a continuation of the first aspect, the invention relates to animal feed additives comprising one or more GH36 polypeptides having alpha-galactosidase activity, wherein the polypeptide having alpha-galactosidase activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3.

In one embodiment, the polypeptide preferably comprises or consists of the amino acid sequence of SEQ ID NO: 3 or an allelic variant thereof; comprises the amino acid sequence of SEQ ID NO: 3 and a N-terminal and/or C-terminal His-tag and/or HQ-tag; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 3. In another embodiment, the polypeptide comprises or consists of amino acids 1 to 721 of SEQ ID NO: 2. In another embodiment, the polypeptide comprises or consists of the mature polypeptide of SEQ ID NO: 2. In another embodiment, the polypeptide comprises or consists of amino acids 1 to 721 of SEQ ID NO: 3. In an embodiment, the polypeptide has been isolated.

In a continuation of the first aspect, the invention relates to animal feed additives comprising one or more GH36 polypeptides having alpha-galactosidase activity, wherein the polypeptide having alpha-galactosidase activity encoded by a polynucleotide that hybridizes under high or very high stringency conditions with (i) the mature polypeptide coding sequence of SEQ ID NO: 1, (ii) the cDNA sequence thereof, or (iii) the full-length complement of (i) or (ii) (Sambrook et al., 1989, Molecular Cloning, *A Laboratory Manual*, 2d edition, Cold Spring Harbor, New York). In an embodiment, the polypeptide has been isolated.

In a continuation of the first aspect, the invention relates to animal feed additives comprising one or more GH36 polypeptides having alpha-galactosidase activity, wherein the polypeptide having alpha-galactosidase activity encoded by a polynucleotide having a sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In one embodiment of the first aspect of the invention, the polypeptide has improved gastric stability compared to control (wherein control is defined as SEQ ID NO: 4). In an embodiment, the gastric stability is measured as the half-life at 40° C. pH3 with 0.1 mg/ml pepsin. In an embodiment, gastric stability is measured as described in example 4 herein. In a further embodiment, the polypeptide has a half-life of at least 90 minutes, such as 2 hours, 3 hours or 4 hours.

In one embodiment of the first aspect of the invention, the polypeptide has increased alpha-galactosidase activity compared to control (wherein control is defined as SEQ ID NO: 4). In one embodiment, activity is measured using 4-nitrophenyl α-D-galactopyranoside as substrate.

In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the polypeptide has an activity of at least 100000 (mOD/min)/(mg/ml), such as at least 150000, at least 200000, at least 250000, or at least 300000 (mOD/min)/(mg/ml) using 4-nitrophenyl α-D-galactopyranoside as substrate. In an embodiment, the polypeptide has at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3 (as determined using 4-nitrophenyl α-D-galactopyranoside as substrate).

In a continuation of the first aspect, the invention relates to animal feed additives comprising variants of SEQ ID NO: 3, wherein the variant of SEQ ID NO: 3 has alpha-galactosidase activity and comprises one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 3 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions in SEQ ID NO: 3 is not more than 10, e.g., 1, 2, 3, 4, 5, 6, 7, 8, 9 or 10. In a further embodiment, the number of conservative substitutions in SEQ ID NO: 3 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; AtoG, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-galactosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

In one embodiment of the first aspect of the invention, the variant has improved gastric stability compared to control (wherein control is defined as SEQ ID NO: 4). In an embodiment, the gastric stability is measured as the half-life at 40° C. pH3 with 0.1 mg/ml pepsin. In an embodiment, gastric stability is measured as described in example 4 herein. In a further embodiment, the variant has a half-life of at least 90 minutes, such as 2 hours, 3 hours or 4 hours.

In one embodiment of the first aspect of the invention, the variant has increased alpha-galactosidase activity compared to control (wherein control is defined as SEQ ID NO: 4). In one embodiment, activity is measured using 4-nitrophenyl α-D-galactopyranoside as substrate. In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the variant has an activity of at least 100000 (mOD/min)/ (mg/ml), such as at least 150000, at least 200000, at least 250000, or at least 300000 (mOD/min)/(mg/ml) using 4-nitrophenyl α-D-galactopyranoside as substrate. In an embodiment, the variant has at least 40%, such as at least 50%, at least 60%, at least 70%, at least 75%, at least 80%, at least 85%, at least 90%, at least 95% or at least 100% of the alpha-galactosidase activity of the variant of SEQ ID NO: 3 (as determined using 4-nitrophenyl α-D-galactopyranoside as substrate).

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Polypeptides Having Alpha-Galactosidase Activity

In a second aspect, the invention relates to polypeptides having alpha-galactosidase activity having at least 96.5%, e.g., at least 97%, at least 97.5%, at least 98%, at least 98.5%, at least 99%, at least 99.5%, or 100% sequence identity to the mature polypeptide of SEQ ID NO: 2. In one embodiment, the polypeptides differ by up to 27 amino acids, e.g., between 1 and 27 amino acids, such as 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26 or 27 amino acids from the mature polypeptide of SEQ ID NO: 2.

In an embodiment, the polypeptide releases at least 14 g, such as at least 14.5 g, at least 15 g, at least 16 g, at least 17 g, at least 18 g, at least 19 g, at least 20 g or at least 22 g galactose per kg soybean meal when performed under the reaction conditions 20 mg polypeptide per kg soybean meal in 10% w/v 0.1M citric acid-phosphate buffer pH 6.5 incubating at 4°° C. for 2 hours.

In a continuation of the second aspect, the invention relates to polypeptides having alpha-galactosidase activity having at least 96.5%, e.g., at least 97%, at least 97.5%, at least 98%, at least 98.5%, at least 99%, at least 99.5%, or 100% sequence identity to SEQ ID NO: 3. In one embodiment, the polypeptides differ by up to 27 amino acids, e.g., between 1 and 27 amino acids, such as 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26 or 27 amino acids from the mature polypeptide of SEQ ID NO: 3.

In one embodiment, the polypeptide preferably comprises or consists of the amino acid sequence of SEQ ID NO: 3 or an allelic variant thereof; comprises the amino acid sequence of SEQ ID NO: 3 and a N-terminal and/or C-terminal His-tag and/or HQ-tag; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 3. In another embodiment, the polypeptide comprises or consists of amino acids 1 to 721 of SEQ ID NO: 2. In another embodiment, the polypeptide comprises or consists of the mature polypeptide of SEQ ID NO: 2. In another embodiment, the polypeptide comprises or consists of amino acids 1 to 721 of SEQ ID NO: 3. In an embodiment, the polypeptide has been isolated.

In a continuation of the second aspect, the invention relates to a polypeptide having alpha-galactosidase activity encoded by a polynucleotide having a sequence identity to the mature polypeptide coding sequence of SEQ ID NO: 1 of at least 96.5%, e.g., at least 97%, at least 97.5%, at least 98%, at least 98.5%, at least 99%, at least 99.5%, or 100%. In a further embodiment, the polypeptide has been isolated.

In a continuation of the second aspect, the invention relates to variants of SEQ ID NO: 3 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 27, e.g., 1, 2, 3, 4, 5, 6, 7, 8, 9, 10, 11, 12, 13, 14, 15, 16, 17, 18, 19, 20, 21, 22, 23, 24, 25, 26 or 27. In another embodiment, the number of positions comprising one or more amino acid substitutions, and/or one or more amino acid deletions, and/or one or more amino acid insertions or any combination thereof in SEQ ID NO: 3 is between 1 and 25, such as 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions in SEQ ID NO: 3 is not more than 10, e.g., 1, 2, 3, 4, 5, 6, 7, 8, 9 or 10. In a further embodiment, the number of conservative substitutions in SEQ ID NO: 3 is not more than 10, e.g., 1, 2, 3, 4, 5, 6, 7, 8, 9 or 10. Examples of amino acid changes, conservative substitutions and fusion peptides are described in the first aspect herein.

Granules Comprising Polypeptides Having Alpha-Galactosidase Activity

In a third aspect, the invention relates to a granule comprising a GH36 polypeptide having having alpha-galactosidase activity, wherein the polypeptide is selected from the group consisting of:
(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
(b) a variant of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a polypeptide comprising the polypeptide of (a) or (b) and a N-terminal and/or C-terminal His-tag and/or HQ-tag;
(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
(e) a fragment of the polypeptide of (a) or (b) having alpha-galactosidase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the third aspect of the invention, the polypeptide has improved gastric stability compared to control (wherein control is defined as SEQ ID NO: 4). In an embodiment, the gastric stability is measured as the half-life at 40° C. pH3 with 0.1 mg/ml pepsin.

In an embodiment, gastric stability is measured as described in example 4 herein. In a further embodiment, the polypeptide has a half-life of at least 90 minutes, such as 2 hours, 3 hours or 4 hours.

In one embodiment of the third aspect of the invention, the polypeptide has increased alpha-galactosidase activity compared to control (wherein control is defined as SEQ ID NO: 4). In one embodiment, activity is measured using 4-nitrophenyl α-D-galactopyranoside as substrate.

In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the polypeptide has an activity of at least 100000 (mOD/min)/(mg/ml), such as at least 150000, at least 200000, at least 250000, or at least 300000 (mOD/min)/(mg/ml) using 4-nitrophenyl α-D-galactopyranoside as substrate. In an embodiment, the polypeptide has at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3 (as determined using 4-nitrophenyl α-D-galactopyranoside as substrate).

In one embodiment of the third aspect of the invention, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment of the third aspect of the invention, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment of the third aspect of the invention, the granule comprises a core particle and one or more coatings. In a preferred embodiment, the coating comprises salt and/or wax and/or flour. Preferred formulations are disclosed in the formulation section below.

In one embodiment of the third aspect of the invention, the granule comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment of the third aspect of the invention, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Liquid formulations comprising polypeptides Having Alpha-galactosidase Activity

In a fourth aspect, the invention relates to a liquid formulation comprising one or more GH36 polypeptides having alpha-galactosidase activity, wherein the liquid formulation comprises:

(A) 0.001% to 25% w/w of polypeptide having alpha-galactosidase activity wherein the polypeptide having alpha-galactosidase activity is selected from the group consisting of:
 (a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
 (b) a variant of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (c) a polypeptide comprising the polypeptide of (a) or (b) and a N-terminal and/or C-terminal His-tag and/or HQ-tag;
 (d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and
 (e) a fragment of the polypeptide of (a) or (b) having alpha-galactosidase activity and having at least 90% of the length of the mature polypeptide; and
(B) water.

In one embodiment, the liquid formulation comprises 20%-80% polyol. In one embodiment, the liquid formulation comprises 0.001% to 2.0% w/w preservative.

In one embodiment, the invention relates to a liquid formulation comprising one or more GH36 polypeptides having alpha-galactosidase activity, wherein the liquid formulation comprises:

(A) 0.001% to 25% w/w of polypeptide having alpha-galactosidase activity wherein the polypeptide having alpha-galactosidase activity is selected from the group consisting of:
 (a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
 (b) a variant of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(c) a polypeptide comprising the polypeptide of (a) or (b) and a N-terminal and/or C-terminal His-tag and/or HQ-tag;

(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having alpha-galactosidase activity and having at least 90% of the length of the mature polypeptide; and (B) 20% to 80% w/w of polyol;

(C) 0.001% to 2.0% w/w preservative; and (D) water.

In one embodiment of the fourth aspect of the invention, the polypeptide has improved gastric stability compared to control (wherein control is defined as SEQ ID NO: 4). In an embodiment, the gastric stability is measured as the half-life at 40° C. pH3 with 0.1 mg/ml pepsin.

In an embodiment, gastric stability is measured as described in example 4 herein. In a further embodiment, the polypeptide has a half-life of at least 90 minutes, such as 2 hours, 3 hours or 4 hours.

In one embodiment of the fourth aspect of the invention, the polypeptide has increased alpha-galactosidase activity compared to control (wherein control is defined as SEQ ID NO: 4). In one embodiment, activity is measured using 4-nitrophenyl α-D-galactopyranoside as substrate.

In one embodiment, activity is measured using 4-nitrophenyl α-D-galactopyranoside as substrate (1 mg/ml in 100 mM MES buffer pH 7.0±0.05, prepared immediately before use) as substrate by measuring the absorbance of released pNP in the buffer at 405 nm for 5 minutes as function of time at room temperature (typically 23° C.). In an embodiment, activity is measured as described in example 3 herein. In an embodiment, the polypeptide has an activity of at least 100000 (mOD/min)/(mg/ml), such as at least 150000, at least 200000, at least 250000, or at least 300000 (mOD/min)/(mg/ml) using 4-nitrophenyl α-D-galactopyranoside as substrate. In an embodiment, the polypeptide has at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3 (as determined using 4-nitrophenyl α-D-galactopyranoside as substrate).

In one embodiment of the fourth aspect of the invention, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment of the fourth aspect of the invention, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment of the fourth aspect of the invention, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment of the fourth aspect of the invention, the preservative is selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassion benzoate or any combination thereof.

In one embodiment of the fourth aspect of the invention, the liquid formulation comprises 0.01% to 25% w/w polypeptide having alpha-galactosidase activity, preferably 0.05% to 20% w/w polypeptide having alpha-galactosidase activity, more preferably 0.2% to 15% w/w polypeptide having alpha-galactosidase activity, more preferably 0.5% to 15% w/w polypeptide having alpha-galactosidase activity or most preferably 1.0% to 10% w/w polypeptide having alpha-galactosidase activity.

In one embodiment, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment of the fourth aspect of the invention, the liquid formulation comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacte-*

*rium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

Sources of Polypeptides Having alpha-galactosidase Activity A polypeptide having alpha-galactosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the polypeptide is from a fungus of the class Eurotiomycetes, such as from the order Eurotiales, or from the family Aspergillaceae, or from the genus *Penicillium* or from the species *Penicillium pseudopulvillorum*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), Rhizomucormiehei aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMIR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Penicillium* cell. In another aspect, the cell is a *Penicillium pseudopulvillorum* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides alpha-galactosidase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the alpha-galactosidase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the composition comprises one or more polypeptides of the second aspect of the invention and one or more formulating agents, as described below.

The compositions may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The compositions may further comprise one or more microbes. In an embodiment, the microbe is selected from the group consisting of Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococsus acidilactici, Pediococcus sp., Propionibacterium thoenii, Propionibacterium sp. and Streptococcus sp. or any combination thereof.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the alpha-galactosidase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the alpha-galactosidase of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer.

A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H20), zinc sulfate heptahydrate (ZnSO4.7H20), sodium phosphate dibasic heptahydrate (Na2HPO4.7H20), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the alpha-galactosidase of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:

(a) a core comprising an alpha-galactosidase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Plant Based Material

In an embodiment, the plant based material is from the taxonomic subclass rosids such as the taxonomic order Fabales or the the taxonomic order Brassicales.

In one embodiment, the plant based material from is from the family Fabaceae, such as the subfamilies Caesalpinioideae or Mimosoideae or Papilionoideae. In an embodiment, the plant based material from is from the sub-family Papilionoideae, such as the tribe Abreae or Amorpheae or Bossiaeeae or Brongniartieae or Cicereae or Crotalarieae or Dalbergieae or Desmodieae or Dipterygeae or Euchresteae or Fabeae or Galegeae or Genisteae or Hedysareae or Hypocalypteae or Indigofereae or Loteae or Millettieae or Mirbelieae or Phaseoleae or Podalyrieae or Psoraleeae or Robinieae or Sesbanieae or Sophoreae or Swartzieae or Thermopsideae or Trifolieae.

In one embodiment, the plant based material from the sub-family Papilionoideae is from the tribe Phaseoleae, such as the genus *Adenodolichos* or *Alistilus* or *Amphicarpaea* or *Ancistrotropis* or *Apios* or *Atylosia* or *Bionia* or *Bolusafra* or *Butea* or *Cajanus* or *Calopogonium* or *Camptosema* or *Canavalia* or *Centrosema* or *Cleobulia* or *Clitoria* or *Cochlianthus* or *Cochliasanthus* or *Collaea* or *Cologania* or *Condylostylis* or *Cratylia* or *Cymbosema* or *Decorsea* or *Dioclea* or *Dipogon* or *Dolichopsis* or *Dolichos* or *Dumasia* or *Dunbaria* or *Eriosema* or *Erythrina* or *Flemingia* or *Galactia* or *Glycine* or *Hardenbergia* or *Helicotropis* or *Kennedia* or *Lablab* or *Leptospron* or *Macroptilium* or *Macrotyloma* or *Mastersia* or *Mucuna* or *Mysanthus* or *Neonotonia* or *Neorautanenia* or *Nesphostylis* or *Nogra* or *Ophrestia* or *Otoptera* or *Oxyrhynchus* or *Pachyrhizus* or *Paracalyx* or *Phaseolus* or *Phylacium* or *Physostigma* or *Pseudeminia* or *Pseudovigna* or *Psophocarpus* or *Pueraria* or *Ramirezella* or *Rhodopis* or *Rhynchosia* or *Shuteria* or *Sigmoidotropis* or *Sinodolichos* or *Spathionema* or *Spatholobus* or *Sphenostylis* or *Strongylodon* or *Strophostyles* or *Teramnus* or *Teyleria* or *Vandasina* or *Vatovaea* or *Vigna* or *Wajira*.

In one embodiment, the plant based material from the sub-family Papilionoideae is from the genus Glycine, such as the species Glycine aff. *tabacina* or *Glycine albicans* or *Glycine aphyonota* or *Glycine arenaria* or *Glycine argyrea* or *Glycine canescens* or *Glycine clandestina* or *Glycine curvata* or *Glycine cyrtoloba* or Glycine dolichocarpa or *Glycine falcata* or *Glycine gracei* or *Glycine hirticaulis* or *Glycine lactovirens* or *Glycine latifolia* or *Glycine latrobeana* or *Glycine microphylla* or *Glycine peratosa* or *Glycine pindanica* or *Glycine pullenii* or *Glycine rubiginosa* or *Glycine stenophita* or *Glycine syndetika* or *Glycine tabacina* or *Glycine tomentella* or Glycine sp. T1 or Glycine sp. T5 or *Glycine gracilis* or *Glycine max* (soy bean) or *Glycine max* x *Glycine soja* or *Glycine soja* (wild soybean).

In one embodiment, the plant based material from the sub-family Papilionoideae is from the genus *Cajanus* such as the species *Cajanus cajan* (pigeon pea), *Cajanus cajanifolius* and *Cajanus scarabaeoide*.

In one embodiment, the plant based material from the sub-family Papilionoideae is from the genus *Phaseolus*, such as the species *Phaseolus acutifolius* (tepary bean) or *Phaseolus acutifolius* var. *latifolius* or *Phaseolus albescens* or *Phaseolus albiflorus* or *Phaseolus albinervus* or *Phaseolus altimontanus* or *Phaseolus amblyosepalus* or *Phaseolus angustissimus* or *Phaseolus augusti* or *Phaseolus bolivianus* or *Phaseolus campanulatus* or *Phaseolus carteri* or *Phaseolus chiapasanus* or *Phaseolus coccineus* (scarlet runner bean) or *Phaseolus coccineus* subsp. *coccineus* or *Phaseolus coccineus* subsp. *polyanthus* or *Phaseolus costaricensis* or *Phaseolus dasycarpus* or *Phaseolus dumosus* or *Phaseolus esperanzae* or *Phaseolus esquincensis* or *Phaseolus filiformis* (slimjim bean) or *Phaseolus glabellus* or *Phaseolus gladiolatus* or *Phaseolus grayanus* or *Phaseolus hintonii* or *Phaseolus jaliscanus* or *Phaseolus juquilensis* or *Phaseolus laxiflorus* or *Phaseolus leptostachyus* or *Phaseolus lignosus* or *Phaseolus lunatus* (lima bean) or *Phaseolus macrolepis* or *Phaseolus maculatifolius* or *Phaseolus maculatus* (co-colmeca bean) or *Phaseolus maculatus* subsp. *ritensis* or *Phaseolus macvaughii* or *Phaseolus magnilobatus* or *Phaseolus marechalii* or *Phaseolus micranthus* or *Phaseolus microcarpus* or *Phaseolus mollis* or *Phaseolus neglectus* or *Phaseolus nelsonii* or *Phaseolus nodosus* or *Phaseolus novoleonensis* or *Phaseolus oaxacanus* or *Phaseolus oligospermus* or *Phaseolus pachyrrhizoides* or *Phaseolus parvifolius* or *Phaseolus parvulus* or *Phaseolus pauciflorus* or *Phaseolus pedicellatus* or *Phaseolus perplexus* or *Phaseolus persistentus* or *Phaseolus plagiocylix* or *Phaseolus pluriflorus* or *Phaseolus polymorphus* or *Phaseolus polystachios* or *Phaseolus polystachios* subsp. *sinuatus* or *Phaseolus polystachios* subsp. *smilacifolius* or *Phaseolus reticulatus* or *Phaseolus rotundatus* or *Phaseolus salicifolius* or *Phaseolus sonorensis* or *Phaseolus talamancensis* or *Phaseolus tenellus* or *Phaseolus texensis* or *Phaseolus tuerckheimii* or *Phaseolus vulgaris* (French bean) or *Phaseolus vulgaris* var. *aborigineus* or *Phaseolus vulgaris* var. *nanus* or *Phaseolus xanthotrichus* or *Phaseolus xolocotzii* or *Phaseolus zimapanensis*.

In one embodiment, the plant based material from the sub-family Papilionoideae is from the tribe Cicereae, such as the genus *Cicer*, such as the species *Cicer anatolicum* or *Cicer arietinum* (chickpea) or *Cicer bijugum* or *Cicer canariense* or *Cicer chorassanicum* or *Cicer cuneatum* or *Cicer*

*echinospermum* or *Cicer flexuosum* or *Cicer floribundum* or *Cicer graecum* or *Cicer incisum* or *Cicer isauricum* or *Cicerjudaicum* or *Cicer kermanense* or *Cicer macracanthum* or *Cicer microphyllum* or *Cicer montbretii* or *Cicer multijugum* or *Cicer nuristanicum* or *Cicer oxyodon* or *Cicer pinnatifidum* or *Cicer pungens* or *Cicer rechingeri* or *Cicer reticulatum* or *Cicer songaricum* or *Cicer spiroceras* or *Cicer stapfianum* or *Cicer subaphyllum* or *Cicer tragacanthoides* or *Cicer yamashitae*

In one embodiment, the plant based material from the sub-family Papilionoideae is from the tribe Genisteae, such as the genus *Adenocarpus* or *Anarthrophyllum* or *Argyrocytisus* or *Argyrolobium* or *Calicotome* or *Chamaecytisus* or *Cytisophyllum* or *Cytisus* or *Dichilus* or *Echinospartum* or *Erinacea* or *Genista* or *Gonocytisus* or *Hesperolaburnum* or *Laburnum* or *Lembotropis* or *Lupinus* or *Melolobium* or *Petteria* or *Podocytisus* or *Polhillia* or *Retama* or *Sellocharis* or *Spartium* or *Stauracanthus* or *Teline* or *Ulex*

In one embodiment, the plant based material from the sub-family Papilionoideae is from the tribe Fabeae, such as the genus *Lathyrus* or *Lens* or *Pisum* or *Vavilovia* or *Vicia*. In one embodiment, the plant based material from the sub-family Papilionoideae is from the genus *Lens*, such as the species *Lens culinaris* (lentil) or *Lens culinaris* subsp. *culinaris* or *Lens culinaris* subsp. *odemensis* or *Lens culinaris* subsp. *tomentosus* or *Lens cyanea* or *Lens ervoides* or *Lens lamottei* or *Lens nigricans* or *Lens orientalis* (ye bing dou).

In one embodiment, the plant based material from the sub-family Papilionoideae is from the genus *Vicia*, such as the species *Vicia garinensis* or *Vicia sojakii* or *Vicia rechingeri* or *Vicia kurdica* or *Vicia multijuga* or *Vicia akhmaganica* or *Vicia variabilis* or *Vicia variegata* or *Vicia persica* or *Vicia kotschyana* or *Vicia hirta* or *Vicia gregaria* or *Vicia ciceroidea* or *Vicia cappadocica* or *Vicia balansae* or *Vicia aucheri* or *Vicia* sp. '*telaponensis*' or *Vicia venulosa* or *Vicia subvillosa* or *Vicia stenophylla* or *Vicia sicula* or *Vicia sibthorpii* or *Vicia semiglabra* or *Vicia scandens* or *Vicia pinetorum* or *Vicia picta* or *Vicia pectinata* or *Vicia paucifolia* or *Vicia palaestina* or *Vicia onobrychioides* or *Vicia ochroleuca* or *Vicia nataliae* or *Vicia montevidensis* or *Vicia monardii* or *Vicia minutiflora* or *Vicia menziesii* or *Vicia megalotropis* or *Vicia malosana* or *Vicia lunata* or *Vicia leucantha* or *Vicia leavenworthii* or *Vicia larissae* or *Vicia iranica* or *Vicia incana* or *Vicia hololasia* or *Vicia glauca* or *Vicia freyniana* or *Vicia floridana* or *Vicia filicaulis* or *Vicia ferreirensis* or *Vicia exigua* or *Vicia dennesiana* or *Vicia cypria* or *Vicia cretica* or *Vicia costata* or *Vicia claessensii* or *Vicia chaetocalyx* or *Vicia cassia* or *Vicia capreolata* or *Vicia caesarea* or *Vicia biennis* or *Vicia baicalensis* or *Vicia altissima* or *Vicia alpestris* or *Vicia acutifolia* or *Vicia pubescens* or *Vicia cirrhosa* or *Vicia koeieana* or *Vicia ramuliflora* or *Vicia multicaulis* or *Vicia parviflora* or *Vicia vicioides* or *Vicia tenuifolia* or *Vicia orobus* or *Vicia nigra* or *Vicia incisa* or *Vicia epetiolaris* or *Vicia crocea* or *Vicia sparsiflora* or *Vicia nummularia* or *Vicia dichroantha* or *Vicia cassubica* or *Vicia monantha* (bard vetch) or *Vicia cinerea* or *Vicia oroboides* or *Vicia tibetica* or *Vicia caroliniana* (Carolina or wood vetch) or *Vicia disperma* or *Vicia esdraelonensis* or *Vicia pulchella* or *Vicia mexicana* or *Vicia leucophaea* or *Vicia humilis* or *Vicia barbazitae* or *Vicia pyrenaica* or *Vicia qatmensis* or *Vicia lathyroides* or *Vicia cuspidata* or *Vicia dionysiensis* or *Vicia abbreviata* or *Vicia sepium* or *Vicia sericocarpa* or *Vicia noeana* or *Vicia hyrcanica* or *Vicia hybrida* or *Vicia galeata* or *Vicia ciliatula* or *Vicia assyriaca* or *Vicia tigridis* or *Vicia anatolica* or *Vicia sylvatica* or *Vicia dumetorum* or *Vicia mollis* or *Vicia aintabensis* or *Vicia peregrina* or *Vicia lutea* (yellow vetch) or *Vicia grandiflora* or *Vicia articulata* or *Vicia americana* or *Vicia michauxii* or *Vicia vicina* or *Vicia venosa* or *Vicia tetrasperma* or *Vicia ervilia* or *Vicia benghalensis* (purple or winter vetch) or *Vicia angustipinnata* or *Vicia amurensis* or *Vicia unijuga* or *Vicia pseudo-orobus* or *Vicia pisiformis* or *Vicia nipponica* or *Vicia nigricans* or *Vicia linearifolia* or *Vicia japonica* or *Vicia hirticalycina* or *Vicia fauriae* or *Vicia chosenensis* or *Vicia bungei* or *Vicia bifolia* or *Vicia amoena* or *Vicia montbretii* or *Vicia serratifolia* or *Vicia paucijuga* or *Vicia kalakhensis* or *Vicia johannis* or *Vicia hyaeniscyamus* or *Vicia galilaea* or *Vicia eristalioides* or *Vicia bithynica* or *Vicia melanops* or *Vicia ludoviciana* or *Vicia pannonica* or *Vicia narbonensis* or *Vicia villosa* or *Vicia hirsuta* or *Vicia sativa* (spring vetch) or *Vicia faba* (broad bean or fava bean) or *Vicia cracca* (bird vetch).

In one embodiment, the plant based material from the sub-family Papilionoideae is from the genus *Pisum*, such as the species *Pisum abyssinicum* (Abyssinian pea) or *Pisum fulvum* or *Pisum sativum* (pea) or *Pisum sativum* subsp. *asiaticum* or *Pisum sativum* subsp. *elatius* (wild pea) or *Pisum sativum* var. *pumilio* (Syrian fodder pea) or *Pisum sativum* subsp. *jomardii* or *Pisum sativum* subsp. *Sativum* or *Pisum sativum* var. *arvense* or *Pisum sativum* var. *choresmicum* or *Pisum sativum* var. *macrocarpon* (snow pea) or *Pisum sativum* var. *ponderosum* or *Pisum sativum* var. *tibetanicum* or *Pisum sativum* subsp. *transcaucasicum*

In one embodiment, the plant based material from the sub-family Papilionoideae is from the tribe Dalbergieae, such as the genus *Adesmia* or *Aeschynomene* or *Amicia* or *Andira* or *Arachis* or *Brya* or *Bryaspis* or *Cascaronia* or *Centrolobium* or *Chaetocalyx* or *Chapmannia* or *Cranocarpus* or *Cyclocarpa* or *Dalbergia* or *Diphysa* or *Discolobium* or *Etaballia* or *Fiebrigiella* or *Fissicalyx* or *Geissaspis* or *Geoffroea* or *Grazielodendron* or *Humularia* or *Hymenolobium* or *Inocarpus* or *Kotschya* or *Machaerium* or *Maraniona* or *Nissolia* or *Ormocarpopsis* or *Ormocarpum* or *Paramachaerium* or *Peltiera* or *Pictetia* or *Platymiscium* or *Platypodium* or *Poiretia* or *Pterocarpus* or *Ramorinoa* or *Riedeliella* or *Smithia* or *Soemmeringia* or *Steinbachiella* or *Stylosanthes* or *Tipuana* or *Weberbauerella* or *Zornia*.

In one embodiment, the plant based material from the sub-family Papilionoideae is from the genus *Arachis*, such as the species *Appressipila* (amendoim bravo) or *Arachis batizocoi* or *Arachis brevipetiolata* or *Arachis burchellii* or *Arachis burkartii* or *Arachis cardenasii* or *Arachis chiquitana* or *Arachis correntina* or *Arachis cruziana* or *Arachis decora* or *Arachis diogoi* or *Arachis duranensis* or *Arachis duranensis* x *Arachis stenosperma* or *Arachis glabrata* (amendoim-bravo) or *Arachis glabrata* var. *glabrata* or *Arachis glabrata* var. *hagenbeckii* or *Arachis glabrata* x *Arachis hypogaea* or *Arachis glandulifera* or *Arachis guaranitica* or *Arachis helodes* or *Arachis hermannii* or *Arachis hoehnei* or *Arachis hypogaea* (peanut) or *Arachis hypogaea* subsp. *Fastigiata* or *Arachis hypogaea* var. *vulgaris* (Spanish peanut) or *Arachis hypogaea* subsp. *Hypogaea* or *Arachis hypogaea* var. *hirsuta* or *Arachis ipaensis* or *Arachis ipaensis* x *Arachis magna* or *Arachis kempff-mercadoi* or *Arachis kretschmeri* or *Arachis kuhlmannii* or *Arachis linearifolia* or *Arachis lutescens* or *Arachis magna* or *Arachis major* or *Arachis matiensis* or *Arachis microsperma* or *Arachis monticola* or *Arachis palustris* or *Arachis paraguariensis* or *Arachis paraguariensis* subsp. *capibarensis* or *Arachis paraguariensis* subsp. *paraguariensis* or *Arachis pflugeae* or *Arachis pintoi* or *Arachis praecox* or *Arachis pusilla* (amendoim de caracar) or *Arachis repens* or *Arachis rigonii* or *Arachis schinini* or *Arachis simpsonii* or *Arachis*

*stenophylla* or *Arachis stenosperma* or *Arachis stenosperma* x *Arachis cardenasii* or *Arachis sylvestris* (*amendoim do porco*) or *Arachis trinitensis* or *Arachis triseminata* or *Arachis tuberosa* or *Arachis valida* or *Arachis villosa* or *Arachis villosulicarpa* or *Arachis williamsii*.

In one aspect, the plant based material is from the taxonomic order Brassicales, such as the family Brassicaceae, preferably the tribe Brassiceae, more preferably the family *Brassica*.

In one embodiment, the plant based material from the tribe Brassiceae is from the family *Brassica*, such as *Brassica aucheri, Brassica balearica, Brassica barrelieri, Brassica carinata* (Abyssinian mustard), *Brassica carinata* x *Brassica napus, Brassica carinata* x *Brassica rapa, Brassica cretica, Brassica deflexa, Brassica desnottesii, Brassica drepanensis, Brassica elongata, Brassica fruticulosa, Brassica fruticulosa* subsp. *cossoniana, Brassica fruticulosa* subsp. *mauritanica, Brassica fruticulosa* subsp. *rifana, Brassica gravinae, Brassica hilarionis, Brassica* hybrid cultivar, *Brassica incana, Brassica insularis, Brassica insularis* subsp. *insularis, Brassica juncea* (Indian mustard), *Brassica juncea* var. *crassicaulis, Brassica juncea* var. *gemmifera, Brassica juncea* var. *gracilis, Brassica juncea* var. *juncea, Brassica juncea* var. *multiceps, Brassica juncea* var. *multisecta, Brassica juncea* var. napiformis (jie cai ge da), *Brassica juncea* var. *rugosa, Brassica juncea* var. *strumata, Brassica juncea* var. *subintegrifolia, Brassica juncea* var. *tumida* (zha cai), *Brassica juncea* var. *utilis, Brassica macrocarpa, Brassica maurorum, Brassica montana, Brassica napus* (rape), *Brassica napus* subsp. *rapifera* (Swedish turnip), *Brassica napus* var. *napus* (annual rape), *Brassica napus* x *Brassica rapa, Brassica nigra* (black mustard), *Brassica nigra* var. *abyssinica, Brassica oleracea, Brassica oleracea* var. *albiflora, Brassica oleracea* var. *alboglabra* (Chinese kale), *Brassica oleracea* var. *botrytis* (cauliflower), *Brassica oleracea* var. *capitata* (cabbage), *Brassica oleracea* var. *costata* (Bedford cabbage), *Brassica oleracea* var. *gemmifera* (Brussels sprouts), *Brassica oleracea* var. *gongylodes* (kohlrabi), *Brassica oleracea* var. *italica* (asparagus broccoli), *Brassica oleracea* var. *medullosa* (marrow-stem kale), *Brassica oleracea* var. *oleracea, Brassica oleracea* var. *ramosa* (branching bush kale), *Brassica oleracea* var. *sabauda, Brassica oleracea* var. *viridis* (kale), *Brassica oleracea* x *Brassica rapa* subsp. *pekinensis, Brassica oxyrrhina, Brassica procumbens, Brassica rapa* (field mustard), *Brassica rapa* subsp. *chinensis* (bok-choy), *Brassica rapa* var. *parachinensis* (cai xin), *Brassica rapa* var. *purpuraria* (purple stem mustard), *Brassica rapa* subsp. *narinosa, Brassica rapa* subsp. *nipposinica* (mizuna), *Brassica rapa* var. *perviridis* (kabuna), *Brassica rapa* subsp. *oleifera* (biennial turnip rape), *Brassica rapa* (Nippo-oleifera Group), *Brassica rapa* subsp. *pekinensis* (Chinese cabbage), *Brassica rapa* subsp. *rapa* (turnip), *Brassica rapa* var. *oleifera, Brassica rapa* x *Brassica nigra, Brassica repanda, Brassica repanda* subsp. *baldensis, Brassica repanda* subsp. *blancoana, Brassica repanda* subsp. *cadevallii, Brassica repanda* subsp. *confusa, Brassica repanda* subsp. *glabrescens, Brassica repanda* subsp. *gypsicola, Brassica repanda* subsp. *latisiliqua, Brassica repanda* subsp. *maritima, Brassica repanda* subsp. *repanda, Brassica repanda* subsp. *saxatilis, Brassica rupestris, Brassica ruvo* (broccoletto), *Brassica souliei, Brassica souliei* subsp. *amplexicaulis, Brassica spinescens, Brassica tournefortii, Brassica villosa* or *Brassica villosa* subsp. *Bivoniana*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Animal Feed and Animal Feed Additives

The present invention also relates to animal feed compositions and animal feed additives comprising one or more alpha-galactosidases of the invention. In an embodiment, the animal feed or animal feed additive comprises a formulating agent and one or more alpha-galactosidases of the invention. In a further embodiment, the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one alpha-galactosidase as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

The animal feed composition of the invention may also contain insect protein, such as protein from mealworm, housefly or black soldier fly larvae, typically in meal form. Insect meal may replace fishmeal entirely or in part, and thus may constitute 0-10% of the total feed.

In still further particular embodiments, the animal feed composition of the invention contains 0-80% maize; and/or 0-80% sorghum; and/or 0-70% wheat; and/or 0-70% barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Brassicaceae, Amaranthaceae, and Poaceae, such as soybean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Amaranthaceae, e.g. beet, sugar beet, spinach or quinoa. Other examples of vegetable protein sources are rapeseed, crambe and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) alpha-galactosidase/enzyme preparation may also be added before or during the feed ingredient step. Typically a liquid alpha-galactosidase/enzyme preparation comprises the alpha-galactosidase of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the alpha-galactosidase can be prepared by freezing a mixture of liquid enzyme solution with a bulking agent such as ground soybean meal, and then lyophilizing the mixture.

In an embodiment, the animal feed or animal feed additive comprises one or more additional enzymes. In an embodiment, the animal feed comprises one or more microbes. In an embodiment, the animal feed comprises one or more vitamins. In an embodiment, the animal feed comprises one or more minerals. In an embodiment, the animal feed comprises one or more amino acids. In an embodiment, the animal feed comprises one or more other feed ingredients.

In another embodiment, the animal feed or animal feed additive comprises the polypeptide of the invention, one or more formulating agents and one or more additional enzymes. In an embodiment, the animal feed or animal feed additive comprises the polypeptide of the invention, one or more formulating agents and one or more microbes. In an embodiment, the animal feed comprises the polypeptide of the invention, one or more formulating agents and one or more vitamins. In an embodiment, the animal feed or animal feed additive comprises one or more minerals. In an embodiment, the animal feed or animal feed additive comprises the polypeptide of the invention, one or more formulating agents and one or more amino acids. In an embodiment, the animal feed or animal feed additive comprises the polypeptide of the invention, one or more formulating agents and one or more other feed ingredients.

In a further embodiment, the animal feed or animal feed additive comprises the polypeptide of the invention, one or more formulating agents and one or more components selected from the list consisting of: one or more additional enzymes; one or more microbes; one or more vitamins; one or more minerals; one or more amino acids; and one or more other feed ingredients.

In an embodiment, the animal feed additive comprises one or more formulating agents, preferably as described herein below.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

The final enzyme concentration in the diet is within the range of 0.01-200 mg enzyme protein per kg diet, preferably between 0.1-100 mg/kg diet, more preferably 0.5-50 mg, even more preferably 1-25 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; 5-50; 10-30; 20-30; 10-20; 15-25; or 1-10; —all these ranges being in mg alpha-galactosidase protein per kg feed (ppm).

For determining mg alpha-galactosidase protein per kg feed, the alpha-galactosidase is purified from the feed composition, and the specific activity of the purified alpha-galactosidase is determined using a relevant assay (see under alpha-galactosidase activity). The alpha-galactosidase activity of the feed composition as such is also determined using the same assay, and on the basis of these two determinations, the dosage in mg alpha-galactosidase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg alpha-galactosidase protein in feed additives. Of course, if a sample is available of the alpha-galactosidase used for preparing the feed additive or the feed, the specific activity is determined from this sample (no need to purify the alpha-galactosidase from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al, "The carbohydrate-active enzymes database (CAZy) in 2013", *Nucl. Acids Res*. (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectinesterase (EC 3.1.1.11), xylanase (EC 3.2.1.8, EC 3.2.1.136), beta-xylosidase (EC 3.2.1.37), or any combination thereof.

In a particular embodiment, the composition of the invention comprises a galactanase (EC 3.2.1.89) and a beta-galactosidase (EC 3.2.1.23).

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8 or EC 3.2.1.136). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Gallipro®, Gallipro® Max, Probios® Guard, Lactiferm® and Bioplus® (Chr Hansen), PoultryStar®, PoultryStar® sol, PoultryStar® me, AquaStar® (Biomin), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™, Cinergy™ FIT, Biacid™, (Cargill), Digestarom® and Digestarom® DC (Biomin) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

Examples of commercial products are VevoVitall® (DSM Nutritional Products), Amasil®, Luprisil®, Lupro-Grain®, Lupro-Cid®, Lupro-Mix®, Lupro-Mix® NA (BASF), n-Butyric Acid AF (OXEA), Biacid™, Prohacid™ Classic and Prohacid™ Advance™ (Cargill), Biotronic® (Biomin) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca-and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Methods of Releasing Galactose

In another aspect, the invention relates to a method of releasing galactose from plant based material, comprising treating the plant based material with the animal the animal feed or animal feed additive of the first aspect of the invention, the alpha-galactosidase of the second aspect of the invention, the granule of the third aspect of the invention or the liquid formulation of the fourth aspect of the invention.

In one embodiment, the animal feed comprises one or more formulating agents as defined herein. In one embodiment, the animal feed comprises one or more additional enzymes as defined herein. In one embodiment, the animal feed comprises one or more microbes as defined herein. In one embodiment, the animal feed comprises plant based material from the subclass rosids. In a preferred embodiment, the animal feed has been pelleted.

In an embodiment, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Methods of Improving Animal Performance

In another aspect, the invention relates to a method of improving one or more performance parameters of an animal comprising administering to the animal the animal feed or animal feed additive of the first aspect of the invention, the alpha-galactosidase of the second aspect of the invention, the granule of the third aspect of the invention or the liquid formulation of the fourth aspect of the invention.

In a further aspect, the invention relates to a method of improving one or more performance parameters of an animal comprising administering to the animal the animal feed or animal feed additive of the first aspect of the invention or the alpha-galactosidase of the second aspect of the invention and plant based material, such that the plant based material is administered together or separately with the polypeptide of the invention.

In one embodiment, the term 'improving one or more performance parameters of an animal' means that there is an increase in body weight gain. In another embodiment, the term 'improving one or more performance parameters of an animal' means that there is an improved feed conversion ratio. In a further embodiment, 'the term 'improving one or more performance parameters of an animal' means that there is an increased feed efficiency. In a further embodiment, the term 'improving one or more performance parameters of an animal' means that there is an increase in body weight gain and/or an improved feed conversion ratio and/or an increased feed efficiency.

In one embodiment, the animal feed comprises one or more formulating agents as defined herein. In one embodiment, the animal feed comprises one or more additional enzymes as defined herein. In one embodiment, the animal feed comprises one or more microbes as defined herein. In one embodiment, the animal feed comprises plant based material from the subclass rosids. In a preferred embodiment, the animal feed has been pelleted.

In an embodiment, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Method for Improving the Nutritional Value of Animal Feed

The term improving the nutritional value of an animal feed means improving the availability of nutrients in the feed. The nutritional values refers in particular to improving the solubilisation and degradation of the raffinose family of oligosaccharides (RFOs), such as the trisaccharide raffinose, the tetrasaccharide stachyose, and the pentasaccharide verbascose, thereby increasing the amount of galactose released which can be utilised by the animal. Consequently, an improved galactose release will result in an improvement of the nutritional value of the feed, thus resulting in increased growth rate and/or weight gain and/or feed conversion (i.e. the weight of ingested feed relative to weight gain).

Thus the invention further relates to a method for improving the nutritional value of an animal feed comprising treating the animal feed with an animal feed or animal feed additive of the first aspect of the invention, the alpha-galactosidase of the second aspect of the invention, the alpha-galactosidase of the second aspect of the invention, the granule of the third aspect of the invention or the liquid formulation of the fourth aspect of the invention. In an embodiment, the animal feed will have improved nutrient digestibility.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Method for Reducing the Anitnutritional Effects of an Animal Feed An excessive amount of oligosaccharides in the hindgut can result in antinutritional effects due to flatulence production. By reducing the amount of oligosaccharide fermentation, the antinutritional effects of some animal feeds can be reduced resulting in improved gut and animal health.

Thus the invention further relates to a method for reducing the anitnutritional effects of an animal feed comprising adding to the feed the alpha-galactosidase of the second aspect of the invention, the granule of the third aspect of the invention or the liquid formulation of the fourth aspect of the invention.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Methods of Preparing an Animal Feed

In another aspect, the invention relates to a method of preparing an animal feed, comprising mixing the animal feed additive of the first aspect of the invention, the alpha-galactosidase of the second aspect of the invention, the granule of the third aspect of the invention or the liquid formulation of the fourth aspect of the invention with plant based material.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Uses

The present invention is also directed to methods for using the polypeptides having alpha-galactosidase activity, or compositions thereof, for e.g. animal feed. The present invention is also directed to processes for using the polypeptides having alpha-galactosidase activity, or compositions thereof, such as e.g. those described below.

Use in Animal Feed

The present invention is also directed to methods for using the alpha-galactosidases of the invention in animal feed.

The term animal includes all animals. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

In the use according to the invention the alpha-galactosidases can be fed to the animal before, after, or simultaneously with the diet. The latter is preferred.

In a particular embodiment, the alpha-galactosidase, in the form in which it is added to the feed, or when being included in a feed additive, is well-defined. Well-defined means that the alpha-galactosidase preparation is at least 50% pure as determined by Size-exclusion chromatography (see Example 12 of WO 01/58275). In other particular embodiments the alpha-galactosidase preparation is at least 60, 70, 80, 85, 88, 90, 92, 94, or at least 95% pure as determined by this method.

A well-defined alpha-galactosidase preparation is advantageous. For instance, it is much easier to dose correctly to the feed a alpha-galactosidase that is essentially free from interfering or contaminating other alpha-galactosidases. The term dose correctly refers in particular to the objective of obtaining consistent and constant results, and the capability of optimizing dosage based upon the desired effect.

For the use in animal feed, however, the alpha-galactosidase need not be that pure; it may e.g. include other enzymes, in which case it could be termed an alpha-galactosidase preparation.

The alpha-galactosidase preparation can be (a) added directly to the feed, or (b) it can be used in the production of one or more intermediate compositions such as feed additives or premixes that is subsequently added to the feed (or used in a treatment process). The degree of purity described above refers to the purity of the original alpha-galactosidase preparation, whether used according to (a) or (b) above.

Preferred Embodiments of the Invention

Preferred embodiments of the invention are described in the set of items below.

1. An animal feed additive comprising one or more GH36 polypeptides having alpha-galactosidase activity selected from the group consisting of:
   (a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;

(b) a polypeptide encoded by a polynucleotide that hybridizes under high stringency conditions, or very high stringency conditions with
   (i) the mature polypeptide coding sequence of SEQ ID NO: 1,
   (ii) the cDNA sequence thereof, or
   (iii) the full-length complementary strand of (i) or (ii);
(c) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
(d) a variant of the polypeptide selected from the group consisting of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41 42, 43, 44, 45, 46, 47, 48, 49 or 50 positions;
(e) a polypeptide comprising the polypeptide of (a), (b), (c) or (d) and a N-terminal and/or C-terminal His-tag and/or HQ-tag;
(f) a polypeptide comprising the polypeptide of (a), (b), (c) or (d) and a N-terminal and/or C-terminal extension of up to 10 amino acids, e.g. 1, 2, 3, 4, 5, 6, 7, 8, 9 or 10 amino acids; and
(g) a fragment of the polypeptide of (a), (b), (c) or (d) having alpha-galactosidase activity and having at least 90% of the length of the mature polypeptide.

2. The animal feed additive of item 1 wherein the polypeptide has improved gastric stability compared to control.
3. The animal feed additive of item 2 wherein control is defined as SEQ ID NO: 4.
4. The animal feed additive of any of items 2 to 3 wherein gastric stability is measured as the half-life at 40° C. pH3 with 0.1 mg/ml pepsin.
5. The animal feed additive of item 1 wherein the polypeptide has a half-life of at least 90 minutes, such as at least 2 hours, 3 hours or at least 4 hours.
6. The animal feed additive of item 5 wherein half-life is measured at 40° C. pH3 with 0.1 mg/ml pepsin.
7. The animal feed additive of any of items 1 to 6 wherein the polypeptide has increased alpha-galactosidase activity compared to control.
8. The animal feed additive of item 7 wherein control is defined as SEQ ID NO: 4.
9. The animal feed additive of any of items 7 to 8 wherein alpha-galactosidase activity is measured using 4-nitrophenyl α-D-galactopyranoside as substrate.
10. The animal feed additive of any of items 7 to 9 wherein alpha-galactosidase activity is at least 100000 (mOD/min)/(mg/ml), such as at least 150000, at least 200000, at least 250000, or at least 300000 (mOD/min)/(mg/ml).
11. The animal feed additive of any of items 1 to 6, wherein the polypeptide has at least 40%, such as at least 50%, at least 60%, at least 70%, at least 75%, at least 80%, at least 85%, at least 90%, at least 95% or at least 100% of the alpha-galactosidase activity of the polypeptide of SEQ ID NO: 3.
12. The animal feed additive of item 11 wherein alpha-galactosidase activity is measured using 4-nitrophenyl α-D-galactopyranoside as substrate.
13. The animal feed additive of any of items 1 to 12 wherein the polypeptide comprises or consists of amino acids 1 to 721 of SEQ ID NO: 2 or amino acids 1 to 721 of SEQ ID NO: 3.
14. The animal feed additive of any of items 1 to 13 further comprising one or more components selected from the list consisting of:
   one or more vitamins;
   one or more minerals;
   one or more amino acids;
   one or more prebiotics;
   one or more phytogenics;
   one or more organic acids; and one or more other feed ingredients.
15. The animal feed additive of any of items 1 to 14 further comprising one or more formulating agents.
16. The animal feed additive of item 15, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.
17. The animal feed additive of any of items 1 to 16 further comprising one or more additional enzymes.
18. The animal feed additive of item 17 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.
19 The animal feed additive of any of items 1 to 18 further comprising one or more microbes.
20. The animal feed additive of item 19, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediocoesus acidilactici, Pediococcus* sp., *Propionibacterium thoenii, Propionibacterium* sp. and *Streptococcus* sp. or any combination thereof.
21. An isolated polypeptide having alpha-galactosidase activity, selected from the group consisting of:
   (a) a polypeptide having at least 96.5%, e.g., at least 97%, at least 97.5%, at least 98%, at least 98.5%, at least 99%, at least 99.5%, or 100% sequence identity to the polypeptide of SEQ ID NO: 3;
   (b) a polypeptide encoded by a polynucleotide having at least 96.5%, e.g., at least 97%, at least 97.5%, at least 98%, at least 98.5%, at least 99%, at least 99.5%, or 100% sequence identity to the mature polypeptide coding sequence of SEQ ID NO: 1;

(c) a variant of the polypeptide selected from the group consisting of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 22, 23, 24, 25, 26 or27 positions;

(d) a polypeptide comprising the polypeptide of (a), (b) or (c) and a N-terminal and/or C-terminal His-tag and/or HQ-tag;

(e) a polypeptide comprising the polypeptide of (a), (b) or (c) and a N-terminal and/or C-terminal extension of up to 10 amino acids, e.g. 1, 2, 3, 4, 5, 6, 7, 8, 9 or 10 amino acids; and (f) a fragment of the polypeptide of (a), (b) or (c) having alpha-galactosidase activity and having at least 90% of the length of the mature polypeptide.

22. The polypeptide of item 21, wherein the polypeptide comprises or consists of amino acids amino acids 1 to 721 of SEQ ID NO: 2 or amino acids 1 to 721 of SEQ ID NO: 3.

23. A composition comprising the polypeptide of any of items 21 to 22.

24. The composition of item 23 further comprising one or more formulating agents.

25. The composition of item 24, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

26. A granule comprising a GH36 polypeptide having alpha-galactosidase activity, wherein the polypeptide is selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;

(b) a variant of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 32, 33, 34, 35, 36, 37, 38, 39, 40, 41 42, 43, 44, 45, 46, 47, 48, 49 or 50 positions;

(c) a polypeptide comprising the polypeptide of (a) or (b) and a N-terminal and/or C-terminal His-tag and/or HQ-tag;

(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having alpha-galactosidase activity and having at least 90% of the length of the mature polypeptide.

27. A granule comprising the animal feed additive of any of items 1 to 20, one or more polypeptides of any of items 21 to 22 or the composition of any of items 23 to 25.

28. The granule of any of items 26 to 27 wherein the granule is coated.

29. The granule of item 28 wherein the coating comprises a salt and/or wax and/or a flour.

30. A liquid formulation comprising one or more GH36 polypeptides having alpha-galactosidase activity, wherein the liquid formulation comprises:

(A) 0.001% to 25% w/w of polypeptide having alpha-galactosidase activity wherein the polypeptide having alpha-galactosidase activity is selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;

(b) a variant of SEQ ID NO: 3, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 32, 33, 34, 35, 36, 37, 38, 39, 40, 41 42, 43, 44, 45, 46, 47, 48, 49 or 50 positions;

(c) a polypeptide comprising the polypeptide of (a) or (b) and a N-terminal and/or C-terminal His-tag and/or HQ-tag;

(d) a polypeptide comprising the polypeptide of (a) or (b) and a N-terminal and/or C-terminal extension of up to 10 amino acids, e.g. 1, 2, 3, 4, 5, 6, 7, 8, 9 or 10 amino acids; and (e) a fragment of the polypeptide of (a) or (b) having alpha-galactosidase activity and having at least 90% of the length of the mature polypeptide; and (B) water.

31. The liquid formulation of item 30, wherein the polypeptide having alpha-galactosidase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

32. The liquid formulation of any of items 30 to 31, wherein the formulation further comprises 20% to 80% w/w of polyol.

33. The liquid formulation of item 32, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.

34. The liquid formulation of any of items 30 to 33, wherein the formulation further comprises 0.01% to 2.0% w/w preservative.

35. The liquid formulation of item 34, wherein the preservative is selected from the group consisting of sodium sorbate, potassium sorbate, sodium benzoate and potassium benzoate or any combination thereof.

36. The liquid formulation of any of items 30 to 35 further comprising one or more components selected from the list consisting of:
one or more enzymes;
one or more microbes;
one or more vitamins;

one or more minerals;
one or more amino acids;
one or more phytogenics;
one or more prebiotics;
one or more organic acids; and one or more other feed ingredients.
37. A method of preparing an animal feed comprising applying the liquid formulation of any of items 30 to 36 onto plant based material.
38. The method of item 37, wherein the liquid formulation is applied via a spray.
39. The method of any of items 37 to 38, wherein the plant based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
40. The method of any of items 37 to 39, wherein the plant based material is in pelleted form.
41. A pelleted animal feed prepared using the method of any of items 37 to 40.
42. An animal feed comprising plant based material and the animal feed additive of any of items 1 to 20, one or more polypeptides of any of items 21 to 22, the composition of any of items 23 to 25, the granule of any of items 26 to 29 or the liquid formulation of any of items 30 to 36.
43. The animal feed of item 42, wherein the plant based material is from the taxonomic subclass rosids.
44. The animal feed of item 42, wherein the plant based material is from the family Fabaceae, preferably the sub-family Papilionoideae, more preferably from the tribe Phaseoleae, Cicereae, Genisteae, Fabeae, Dalbergieae or Phaseoleae or any combination thereof
45. The animal feed of item 42, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
46. A pelleted animal feed comprising plant based material and the animal feed additive of any of items 1 to 20, one or more polypeptides of any of items 21 to 22, the composition of any of items 23 to 25, the granule of any of items 26 to 29 or the liquid formulation of any of items 30 to 36.
47. The pelleted animal feed of item 46, wherein the plant based material is from the subclass rosids, preferably the family Fabaceae, more preferably the sub-family Papilionoideae or more preferably is from the tribe Phaseoleae, Cicereae, Genisteae, Fabeae, Dalbergieae or Phaseoleae or any combination thereof.
48. The pelleted animal feed of item 46, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
49. A method of releasing galactose from plant based material, comprising treating the plant based material with the animal feed additive of any of items 1 to 20, one or more polypeptides of any of items 21 to 22, the composition of any of items 23 to 25, the granule of any of items 26 to 29 or the liquid formulation of any of items 30 to 36.
50. A method of improving one or more performance parameters of an animal comprising administering to one or more animals the animal feed additive of any of items 1 to 20, one or more polypeptides of any of items 21 to 22, the composition of any of items 23 to 25, the granule of any of items 26 to 29, the liquid formulation of any of items 30 to 36, the animal feed of any of items 42 to 45 or the pelleted animal feed of any of items 41 or 46 to 48.
51. The method of item 50, wherein the performance parameter is selected from the list consisting of body weight gain (BWG), European Production Efficiency Factor (EPEF) and Feed Conversion Ratio (FCR) or any combination thereof.
52. A method for improving the nutritional value of an animal feed comprising plant based material, comprising mixing the plant based material with the animal feed additive of any of items 1 to 20, one or more polypeptides of any of items 21 to 22, the composition of any of items 23 to 25, the granule of any of items 26 to 29 or the liquid formulation of any of items 30 to 36.
53. A method of preparing an animal feed, comprising mixing the animal feed additive of any of items 1 to 20, one or more polypeptides of any of items 21 to 22, the composition of any of items 23 to 25, the granule of any of items 26 to 29 or the liquid formulation of any of items 30 to 36 with plant based material.
54. The methods of any of items 49 to 53, wherein the plant based material is from the taxonomic subclass rosids.
55. The methods of any of items 49 to 53, wherein the plant based material is from the family Fabaceae, preferably the sub-family Papilionoideae, more preferably from the tribe Phaseoleae, Cicereae, Genisteae, Fabeae, Dalbergieae or Phaseoleae or any combination thereof.
56. The methods of any of items 49 to 53, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
57. Use of the animal feed additive of any of items 1 to 20, one or more polypeptides of any of items 21 to 22, the composition of any of items 23 to 25, the granule of any of items 26 to 29, the liquid formulation of any of items 30 to 36, the animal feed of any of items 42 to 45 or the pelleted animal feed of any of items 41 or 46 to 48:
in animal feed;
in animal feed additives;
in the preparation of a composition for use in animal feed;
for improving the nutritional value of an animal feed;
for increasing digestibility of the animal feed;
for improving one or more performance parameters in an animal; and/or for releasing galactose from plant based material.
58 A polynucleotide encoding the polypeptide of any of items 21 to 22.
59. A nucleic acid construct or expression vector comprising the polynucleotide of item 58 operably linked to one or more control sequences that direct the production of the polypeptide in an expression host.

60. A recombinant host cell comprising the polynucleotide of item 58 operably linked to one or more control sequences that direct the production of the polypeptide.
61. A method of producing the polypeptide of any of items 21 to 22, comprising:
    (a) cultivating a cell, which in its wild-type form produces the polypeptide, under conditions conductive for production of the polypeptide; and
    (b) recovering the polypeptide.
62. A method of producing the polypeptide of any of items 21 to 22, comprising:
    (a) cultivating the recombinant host cell of item 60 under conditions conducive for production of the polypeptide; and
    (b) recovering the polypeptide.
63. A transgenic plant, plant part or plant cell transformed with a polynucleotide encoding the polypeptide of any of items 21 to 22.
64. A whole broth formulation or cell culture composition comprising a polypeptide of any of items 21 to 22.

The present invention is further described by the following examples that should not be construed as limiting the scope of the invention.

EXAMPLES

Strains

The alpha-galactosidases were derived from bacterial strains isolated from environmental samples by standard microbiological isolation techniques. Strains were identified and taxonomy was assigned based on DNA sequencing of the 16S ribosomal genes (Table 2).

TABLE 2

Isolation of fungal strain

| Strain | Source | Country | Year | SEQ ID NO of gene | SEQ ID NO of polypeptide |
|---|---|---|---|---|---|
| Penicillium pseudopulvillorum | Soil | Nicaragua | 1949 | 1 | 2 |

Chromosomal DNA isolated from pure cultures of the individual strains with the DNeasy Blood & Tissue Kit from Qiagen (Hilden, Germany) was subjected to full genome sequencing using Illumina technology. Genome sequencing, the subsequent assembly of reads and the gene discovery (i.e. annotation of gene functions) is known to the person skilled in the art and the service can be purchased commercially.

The genome sequence was analyzed for alpha-galactosidases from the CAZY database family GH36 (Lombard et al. The Carbohydrate-active enzymes database CAZy. Nucleic Acids Res 2013, 42:D490-D495.) This analysis identified a gene encoding a putative secreted alpha-galactosidase with the nucleotide sequence given in SEQ ID NO: 1.

Alpha-Galactosidase Assay

Alpha-galactosidase activity can be determined using 4-nitrophenyl α-D-galactopyranoside (product code O-PNPBGAL, available from Megazyme International, Bray, Co. Wicklow, Ireland) as follows.

The enzyme was diluted using 100 mM MES (Sigma) buffer pH 7.0±0.05 in 2-fold dilutions and then the 4-nitrophenyl α-D-galactopyranoside (1 mg/ml in 100 mM MES buffer pH 7.0±0.05, prepared immediately before use) was added in the solution containing the enzyme. The respective galactosidase activity was followed directly in the buffer by measuring the absorbance of released pNP (para-nitro-phenol) at 405 nm for 5 minutes as function of time at room temperature (typically 23° C.). A concentration of 1 mg/mL of enzyme is a good starting point; it will however depend from enzyme to enzyme and their specific activity.

The activity is calculated as the slope of a plot of absorbance versus time (units: mOD/min) using the 1-5 minute time window and the 0-2 absorbance window. The activity can then be converted to specific activity by dividing the activity for the concentration of the enzyme (units: (mOD/min)/(mg/ml)).

Galactose Assay

Introduction

The concentration of galactose monosaccharides in a solution was measured spectrophotometrically after enzymatic hydrolysis of a galactose-rich substrate; soybean meal.

Summarizing, the enzyme(s) were incubated in a 10 w/v % slurry of soybean meal at pH 6.5±0.05 for 2 hours at 40±2° C. The supernatant was then analyzed in an assay based on the Raffinose/Galactose kit from Megazyme (product name K-RAFGA). First α-D-galactose in the supernatant was converted to β-D-galactose with the enzyme galactose mutarotase. Then 1-D-galactose was oxidised by NAD+ to D-galactonic acid in the presence of β-galactose dehydrogenase. The amount of NADH formed in this reaction was stoichiometric with the amount of D-Galactose in the supernatant. NADH concentration was then measured by the increase in absorbance at 340 nm.

Soybean Meal Slurry

A 10 w/v % slurry of soybean meal was prepared from soybean meal milled to a 0.5 mm particle size and 0.1 M citric acid-phosphate buffer, pH 6.5±0.05.

0.1 M citric acid-phosphate buffer, pH 6.5±0.05 was heated to a temperature of approximately 40° C. while stirring. The preheated buffer was then transferred to the soybean meal. The resulting slurry was stirred while being heated (temperature was not monitored at this point—heating was only applied to ensure that temperature would not decrease too much while the slurry stirred). The slurry was then transferred with a pre-wetted wide-bore pipette to the vessel in which it should be incubated. The slurry was pipetted from an approximately central point in the mix. The time elapsed from the mixing of the slurry until transfer to the last incubation vessel was, at most, 15 minutes. Stirring speed was adjusted in such a way that particles were evenly distributed in the slurry.

Dilution of Enzymes

The enzymes were diluted to their desired concentrations in ultrapure water. The concentration to which the enzymes were diluted to was based on the prior concentration of the enzyme in mg enzyme protein per mL (mg EP/mL) and the mass (kg) of dry matter (soybean meal) in each incubation vessel.

$$V_{enzyme}(\text{mL}) = \frac{c_{enzyme}\left(\text{mg}\frac{EP}{\text{mL}}\right)}{m_{SBM}(\text{kg})}$$

D-(+)-galactose standards

A standard curve was prepared from D-(+)-galactose and ultrapure water. A D-(+)-galactose stock was prepared by dissolving D-(+)-galactose in ultrapure water to a final concentration of 250 mg galactose per mL. The stock solution was diluted in a two-fold dilution row to obtain six standards with concentrations of 250, 125, 62.5, 31.25, 15.625 and 7.813 mg galactose per mL.

Incubation of α-Galactosidases on Soybean Meal

The incubation vessels with the 10 w/v % slurry of soybean meal were heated to a stable temperature of 40±2° C. while stirring. When a stable temperature had been achieved, the six D-(+)-galactose standards were added to the incubation vessels to in-vessel concentrations of 5, 2.5, 1.25, 0.625, 0.313 and 0.157 mg galactose per mL incubation volume. Each standard was incubated in duplicates.

The diluted enzymes were then added to their respective incubation vessels in the volumes required to reach their desired concentrations (in mg EP/kg soybean meal). Each enzyme treatment was incubated in triplicates.

Additionally, two times three incubation vessels were included without standards or enzyme treatments as blank treatments to obtain the baseline galactose concentration in the soybean meal slurry.

The incubation vessels were incubated at 40±2° C., while stirring for 2 hours. After incubation the vessels were centrifuged at 1500 g at 5° C. for 15 minutes.

Determination of Galactose Concentration

The supernatants in the now centrifuged incubation vessels were then analyzed in an assay based on the Raffinose/Galactose kit from Megazyme (product name K-RAFGA). Three reagents from the K-RAFGA kit was used in the assay: Assay Buffer (supplied and ready in Bottle 1 in the kit), 1-NAD reagent (supplied in Bottle 2 in the kit, prepared as described in the kit prior to use) and GalDH+GalM solution (supplied in Bottle 3 in the kit, diluted 1:1 in ultrapure water prior to use). All steps described in the following were carried out using an Eppendorf 5075 automated pipetting system.

First the supernatants from the centrifuged incubation vessels were diluted 10 times in 0.1 M citric acid-phosphate buffer, pH 6.5±0.05 (1 part supernatant plus 9 parts 0.1 M citric acid-phosphate buffer, pH 6.5±0.05).

69 µL of each diluted supernatant was then transferred to a new vessel and 34 µL of ultrapure water was added to the diluted supernatants (which will be referred to as assay samples from here on out). Then 69 µL Assay Buffer was added to the assay samples followed by dilution in 687 µL ultrapure water. 34 µL 1-NAD reagent was added to the assay samples, followed by addition of 14 µL GalDH+GalM solution and vigorous mixing.

262 µL of each assay sample was then transferred to a 96 well micro titer plate. Absorbance in each well of the 96 well micro titer plate was measured at 340 nm at 40±2° C. for a duration of 20 minutes or until absorbance in each well had reached a stable level. When a stable absorbance had been reached this stable absorbance was used in later calculations.

Calculation of Galactose Concentration

Absorbance of the assay samples from the galactose standards in the incubation vessels were used as a standard curve (6 standards, 5, 2.5, 1.25, 0.625, 0.313 and 0.157 mg galactose per mL incubation volume, n=2 per standard). An equation for the galactose standard curve was calculated in excel, where y is OD340 and x is galactose concentration in mg galactose per mL incubation volume:

$$OD_{340} = a * c_{gal}\left(\frac{mg}{mL}\right) + b$$

Galactose concentration in mg galactose per mL incubation volume for each sample was then given by:

$$c_{gal}\left(\frac{mg}{mL}\right) = \frac{OD_{340} - b}{a}$$

Galactose concentrations were then calculated on a dry-matter basis (g galactose per kg soybean meal) and are reported in the examples below:

$$c_{gal}\left(\frac{g}{kg}SBM\right) = \frac{c_{gal}\left(\frac{mg}{mL}\right) * V_{sample}(mL)}{m_{SBM}(g)}$$

Example 1: Cloning of GH36 Alpha-Galactosidase (SEQ ID NO: 1)

The alpha-galactosidase with nucleotide sequence SEQ ID NO: 1 and the peptide translation of the protein shown in SEQ ID NO: 2 was PCR amplified from genomic DNA isolated from *Penicillium pseudopulvillorum* and cloned into the expression vector pDAu222 as described in WO 2013024021 using BamHI and XhoI restriction sites.

The sequence of the alpha-galactosidase encoding gene cloned in the expression vector was confirmed and the expression construct was transformed into the *Aspergillus oryzae* strain MT3568 (WO 11/057140) to produce the secreted mature peptide with protein sequence SEQ ID NO: 12. Transformants were selected on acetamide during regeneration from protoplasts and subsequently re-isolated under selection (Christensen et al., 1988, *Biotechnology* 6, 1419-1422 and WO 04/032648).

For production of the recombinant alpha-galactosidase, a single *Aspergillus* transformant was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter.

Example 2: Purification of GH36 Alpha-Galactosidases (SEQ ID NO: 3)

Filtrated broth was adjusted to pH7.0 and filtrated on 0.22 µm PES filter (Nalge Nunc International, Nalgene labware cat #595-4520). Following, the filtrate was added 1.8M ammonium sulphate. The filtrate was loaded onto a Phenyl Sepharose™ 6 Fast Flow column (high sub) (GE Healthcare, Piscataway, N.J., USA) equilibrated with 1.2M ammonium sulphate, 25 mM HEPES pH7.0. After wash with 1.0M ammonium sulphate, the bound proteins were batch eluted with 25 mM HEPES pH 7.0. Fractions were collected and analyzed by SDS-PAGE. The fractions were pooled and applied to a Sephadex™ G-25 (medium) (GE Healthcare, Piscataway, N.J., USA) column equilibrated in 25 mM HEPES pH 7.5. The fractions were applied to a SOURCE™ 15Q (GE Healthcare, Piscataway, N.J., USA) column equilibrated in 25 mM HEPES pH 7 and bound proteins were eluted with 25 mM HEPES pH 7, 1 M sodium chloride over ca. 20CV. Fractions were collected and analyzed by SDS-PAGE.

Example 3: Specific Activity of the GH36 Alpha-Galactosidase of SEQ ID NO: 3

The specific activity of the GH36 alpha-galactosidase of the invention (SEQ ID NO: 3) was measured using the Alpha-Galactosidase Assay as disclosed herein and compared to the activity of the prior art GH36 alpha-galactosidase from *Aspergillus niger* (SEQ ID NO: 4). The results are presented in table 3.

TABLE 3

Specific activity of the GH36 alpha-galactosidases (SEQ ID NO: 3 and 4)

| GH36 alpha-galactosidase | Specific Activity on pNP substrate (mOD/min)/(mg/ml) |
|---|---|
| SEQ ID NO: 3 | 360000 |
| SEQ ID NO: 4 | 85000 |

The GH36 alpha-galactosidase of the invention (SEQ ID NO: 3) is significantly more active in releasing pNP from 4-nitrophenyl α-D-galactopyranoside than the prior art alpha-galactosidase of SEQ ID NO: 4.

Example 4: Gastric Stability of the GH36 Alpha-Galactosidase of SEQ ID NO: 3

Reagents

Pepsin from porcine gastric mucosa (Sigma P7000) diluted in 50 mM glycine buffer pH 3.00±0.05

Stressing buffer 1: 50 mM glycine pH 3.00±0.05

Stressing buffer 2: 50 mM glycine pH 3.00±0.05+0.1 mg/mL pepsin

Stressing buffer 3: 100 mM MES pH 7.00±0.05

Recovery buffer: 100 mM MES pH 7.00±0.05

Substrate working solution: 1 mg/mL α-pNP diluted in 100 mM MES pH 7.00±0.05. This working solution is made immediately before use.

Procedure

160 µL of stressing buffer 1, stressing buffer 2 or stressing buffer 3 was added to the wells of a 96 well PCR plate. The PCR plate was incubated at 40° C. for 10 minutes, then 40 µL of the alpha-galactosidase sample to be analyzed was added to the wells containing the stressing buffer. Note that the enzyme was diluted so that the activity in stressing buffer 3 was ~250 mOD/min. After 2, 5, 10, 15, 20, 25 and 30 minutes incubation at 40° C., 20 µL of the stressed enzymes was added to 80 µL of recovery buffer in the wells of a micro titer plate kept at room temperature. 100 µL of substrate working solution was then added to the wells of the micro titer plate. The solution was mixed for 10 seconds at room temperature and absorption at 405 nm was measured every 30 seconds over 5 minutes.

The activity of the α-galactosidase (V0) was calculated as the slope of the time-dependent absorption curve in the 0.0-2.0 OD absorbance window. In order to evaluate the half-life of the enzyme, the activity (V0) was plotted against the incubation time and the data was fitted to an exponential function of the type: $V0(t) = A\, e^{-\lambda t}$, where $V0(t)$ is the activity $V0$ at time t, $A = V0(0)$ is the V0 at time=0 and $\lambda$ is the exponential decay constant (also known as decay rate). The half-life is then evaluated as $T = (\ln(2))/\lambda$.

The results are presented in table 4.

TABLE 4

Specific activity of the GH36 alpha-galactosidases (SEQ ID NO: 3 and 4)

| GH36 alpha-galactosidase | T½ (min) 40 C. pH 3 no pepsin | T½ (min) 40 C. pH 3 with 0.1 mg/ml pepsin |
|---|---|---|
| SEQ ID NO: 3 | Stable | Stable |
| SEQ ID NO: 4 | Stable | 77 ± 1 |

The results show that whilst the prior art alpha-galactanase (SEQ ID NO: 4) is stable at pH3 without any pepsin being present, it decomposes relatively quickly in the presence of 0.1 mg/ml pepsin. In comparison, the alpha-galactanase of the invention (SEQ ID NO: 3) is completely stable both with and without pepsin present.

Example 5: Animal Feed and Animal Feed Additives Comprising an Alpha-Galactosidase Animal Feed Additive A formulation of an alpha-galactosidase of the invention (e.g. SEQ ID NO: 3) containing 0.01 g to 10 g enzyme protein is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:
62.55% Maize
33.8% Soybean meal (50% crude protein)
1.0% Soybean oil
0.2% DL-Methionine
0.22% DCP (dicalcium phosphate)
0.76% CaCO₃ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Liquid Formulation

A liquid formulation of an alpha-galactosidase of the invention (e.g. SEQ ID NO: 3) comprises 0.1% to 10 w/w enzyme protein, 40-60% glycerol, 0.1 to 0.5% sodium benzoate and water. The liquid formulation is sprayed onto the pelleted animal feed described above (in this case the animal feed additive would not include the alpha-galactosidase of the invention present).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An animal feed comprising a plant-based material and a Glycoside Hydrolase 36 (GH36) polypeptide having alpha-galactosidase activity, wherein the GH36 polypeptide has at least 98% sequence identity to the amino acid sequence set forth in SEQ ID NO: 3, and wherein the GH36 polypeptide has improved gastric stability and/or increased alpha-galactosidase activity using 4-nitrophenyl α-D-galactopyranoside as substrate compared to control and is in the form of a granule.

2. The animal feed of claim 1, wherein the plant-based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), pea, soybean meal, full fat soy bean meal, soy protein concentrate (SPC), fermented soybean meal (FSBM) and any combination thereof.

3. The animal feed of claim 1, wherein the plant-based material is soybean or soybean meal.

4. The animal feed of claim 1, wherein the GH36 polypeptide has at least 99% sequence identity to the amino acid sequence set forth in SEQ ID NO: 3.

5. The animal feed of claim 1, wherein the GH36 polypeptide comprises the amino acid sequence set forth in SEQ ID NO: 3.

6. The animal feed of claim 1, wherein the GH36 polypeptide consists of the amino acid sequence set forth in SEQ ID NO: 3.

7. The animal feed of claim 1, wherein the GH36 polypeptide comprises an N-terminal and/or C-terminal His-tag and/or HQ-tag.

8. The animal feed of claim 1, further comprising one or more components selected from the group consisting of:
   one or more vitamins;
   one or more minerals;
   one or more amino acids;
   one or more prebiotics;
   one or more phytogenics;
   one or more organic acids; and
   one or more other feed ingredients.

9. The animal feed of claim 1, further comprising one or more additional enzymes.

10. The animal feed of claim 9, wherein the one or more additional enzymes are selected from the group consisting of acetylxylan esterase, acylglycerol lipase, alpha-amylase, beta-amylase, arabinofuranosidase, cellobiohydrolase, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase and any combination thereof.

11. A method of improving one or more performance parameters of an animal, comprising administering to one or more animals the animal feed of claim 1, wherein the one or more performance parameters are increase in body weight gain, improved feed conversion ratio, or increased feed efficiency.

12. A liquid formulation comprising water, a polyol, and a Glycoside Hydrolase 36 (GH36) polypeptide having alpha-galactosidase activity, wherein the GH36 polypeptide has at least 98% sequence identity to the amino acid sequence set forth in SEQ ID NO: 3, and wherein the GH36 polypeptide has improved gastric stability and/or increased alpha-galactosidase activity using 4-nitrophenyl α-D-galactopyranoside as substrate compared to control.

13. The liquid formulation of claim 12, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 and any combination thereof.

14. The liquid formulation of claim 12, further comprising 0.01% to 2.0% w/w preservative, wherein the preservative is selected from the group consisting of sodium sorbate, potassium sorbate, sodium benzoate and potassium benzoate and any combination thereof.

15. The liquid formulation of claim 12, further comprising one or more components selected from the group consisting of:
 one or more enzymes;
 one or more microbes;
 one or more vitamins;
 one or more minerals;
 one or more amino acids;
 one or more phytogenics;
 one or more prebiotics;
 one or more organic acids; and
 one or more other feed ingredients.

16. A method of preparing an animal feed, comprising applying the liquid formulation of claim 12 to a plant-based material.

17. The method of claim 16, wherein the plant based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), pea, soybean meal, full fat soy bean meal, soy protein concentrate (SPC), fermented soybean meal (FSBM) and any combination thereof.

\* \* \* \* \*